United States Patent
Shimamoto et al.

(10) Patent No.: US 6,472,513 B1
(45) Date of Patent: Oct. 29, 2002

(54) HUMAN GENE RECQ4 ENCODING HELICASE

(75) Inventors: Akira Shimamoto, Kanagawa (JP); Saori Kitao, Kanagawa (JP); Yasuhiro Furuichi, Kanagawa (JP)

(73) Assignee: Agene Research Institute Co., Ltd., Kanagawa (JP)

( * ) Notice: Subject to any disclaimer, the term of this patent is extended or adjusted under 35 U.S.C. 154(b) by 0 days.

(21) Appl. No.: 09/699,135

(22) Filed: Oct. 27, 2000

Related U.S. Application Data

(62) Division of application No. 09/463,702, filed as application No. PCT/JP98/03114 on Jul. 10, 1998, now Pat. No. 6,335,435.

(30) Foreign Application Priority Data

Jul. 25, 1997 (JP) .............................................. 9/200387

(51) Int. Cl.⁷ .............................................. C07K 16/40
(52) U.S. Cl. .............................. 530/388.26; 530/388.1; 530/388.15; 530/388.9; 530/389.1
(58) Field of Search .......................... 530/387.9, 388.1, 530/388.15, 388.26, 389.1

(56) References Cited

U.S. PATENT DOCUMENTS 6,090,620 A  *  7/2000  Fu et al.

OTHER PUBLICATIONS

Puranam et al. Cloning and characterization of RECQL, a potential human homologue of the *Escherichia coli* DNA helicase RecQ, Nov. 1994, J Biol Chem 25;269(47): 29838–45.*
Kuby et al., 1994, Immunology, second edition, pp. 85–96.*
Colman et al, Effects of amino acid sequence changes on antibody–antigen interaction, 1994, A structural view of immune recognition by antibodies, pp. 33–36.*
Skolnick et al, From genes to protein structure and function: novel applications of computational approaches in the genomic era, Jan., 2000, TIBTECH 18: 34–39.*

* cited by examiner

Primary Examiner—Christina Chan
Assistant Examiner—Phuong N. Huynh
(74) Attorney, Agent, or Firm—Gray Cary Ware & Freidenrich LLP

(57) ABSTRACT

A gene encoding: (a) a protein comprising an amino acid sequence of SEQ ID NO: 2; or (b) a protein having deletion, substitution or addition of at least one amino acid residue in the amino acid sequence of SEQ ID NO: 2, which has a helicase activity.

3 Claims, 7 Drawing Sheets

FIG. 2

```
RecQ4          QALEQLGHQAFRPGQERAVMRILSGI-STILYTPTCAQKBLCYQLPABLLYSRRSPCLTLVVSPLLSLMDDQVSGLPPC-LKAACIHSGMTRKQRESVLQK     568
E. coli RecQ   -----FGYQQFRPGQEEIIDTVLSGR-DCLVMPTGGGKSLCYQIPALLNG----LTVVVSPLISLMKDQVDQLQANGVAAACLNSTQTREQQLEVMTG         112
yeast SGS1     ------FRPNQLEAVNATLQGK-DYTVLMPTGGGKSLCIQLPAVVKSGKTHGTTIVTSPLISLMQDQVEHLLNKNIKASMFSSRG-TAEQRRQTF-          765
RecQ1          ------FRPLQLETINVTMAGK-EVTSVMPTGGGKBLCIQIPALCSDG----FTIVICPLLBLMEDQLAVLKQLGISATMLNASSSKEHVKWVHDE          176
Bloom          ------FRPLQLETINVTMAGK-DCPILMPTGGGKSLCYQLPACVSPG---VTVVVSPLRSLLVDQVQKLTSLDIPATYLTGDKTDSEATNIYLQ           752
Werner         ---------QLEAINAALLGE-DCPILMPTGGGKSLCYQLPACVSPG---VTVVSPLRSLLVDQVQKLTSLDIPATYLTGDKTDSEATNIYLQ            631
               CLRMYFGHSSFKPVQWKVIHSVLEERRDNVAVAATGYQKSLCFQIPPYV-GK----IGLVISPLISLMEDQYLQLKMSNIPACFLGSAQSENVLTDI---
                                                                                    Ia RecQ4          IRAAQ--VHVLMLITPEALVGAGG-----LPPAAQLPVAPACTDEAHCISQWSHNFRPCYLRVCKVLRERMGVHCFLGLTATATRRTASDVAQHLAVAEEP    662
E. coli RecQ   CRTGQ--IRLLYIAPERLMLDNFLEH-L-----AHWNPVLLAVDEAHCISOWGHDFRPEYAALGQLRQRFPTL-PFMALTATADDTTRQDIVRLLGLNDPL    204
yeast SGS1     NLFINGLLDLVTISPEMISASEQCKRAISRLYADGKLARITVDEAHCVSNWGHDFRPDYKELKFFKREYPDI-PMIALTATABEQVRMDLIHNLELKEPV    864
RecQ1          MVNKNSELKLLIYVTPEKIAKSKMFMSRLEKAYEARRFTRIAVDEVRCCBQWGHDFRPDYKALGILKRQFPNA-SLIGLTATATNHVLTDAQKILCIEKCF    275
Bloom          LSKKDPIIKILLYVTPEKICASNRLISTLENLYERKLLARFVIDEAHCVSQWGHDFRQDTFRMNMLRQKFPSV-PVMALTATANPRVQKDILTQLKILRPQ    851
Werner         ---KLGKYRIVYVTPE-YCSGN---MGLLQQLEADIGITLIAVDEAHCISEMGHDFRDSFRKLGSLKTALPMV-PIVALTATASSIREDIVRCLNLRNPQ    724
                                                                           II                                  III RecQ4          DLHGPAPVPTNLHLSVSMDRDTDQALLT---LLQGK-RFQNLDSIIIYCNRREDTTRIALLRTCLHAAWVPGSGGRAPKTTAEAYHAGMCSRERRRVQRA    759
E. coli RecQ   IQIBSFDRPNIRYMLMEKFKPLDQLMRY---VQEQ-RGK---SGIIYCNSRLAFVETVAAALQS-KGIS---------AAAYHAGLENNVRADVQEK        283
yeast SGS1     FLKQSFNRTNLYYEVN-KKTKNTIFEICDA-VKS--RFKNQ-TQTTYCHSKFBCECFBAQMQRN-GI---------KCAYHAGMEPDERLSVQKA          945
RecQ1          TFTASFNRPNLYYEVRQKPSNTEDFIEDIVKLING-RYKGQ-SGIIYCFBQKDSEQVTVSLQN-LGIH--------AGAYHANLEPEDKTTVHRK          359
Bloom          VFSMSFNRHRHNLKYYVLPKKPKKVAFDCLEW-IR--KHHPYDSGIIYCLSRRECDTWADTIQRD-GL----------AALAYHAGLSDSARDEVQQK       933
Werner         ITCYGFDRPNL--YLEVRRKTGNILQDLQPFLVKTSSHWEFEGPTIIYCPSRKMTQQYVGELHKL-NLS-----CGTYHAGMSFSTRKDIHHR           809
                                          IV RecQ4          FMQGQ--LRVYVATVYATGWGIDDRPDVRAVLHLGLPTSTESYVQAVGRAGRDGQPAHCHLFLQPQGEDL-RELRRH                             831
E. coli RecQ   FQRDD-LQIVVATVAFGMGINKPNVRFVVHFDIPRNIESYVQETGRAGRDGLPAEAMLFYDPADMAWLRRCLEE                               356
yeast SGS1     WQADE-IQVICATVAFGMGIDKPDVRFVYHFTVPRTLEGYYQETGRAGRDGNYSYCITYFSFRDIRT                                     1011
RecQ1          WSANE-IQVVATVAFGMGIDKPDVRFVIHHSMSKSMENYYQESGRAGRDDMKADCILYYGFGDI                                         423
Bloom          WINQDGCQYICATLAFGMGIDKPDVRFVIHASLPKSVEGTIQEBGRAGRDGEISHCLL                                               991
Werner         FVRDE-IQCVIATIAPGMGINKADIRQVIHYGAPKDMESYIQEIGRAGRDGLQSSCHVLWAPADINLNRHLLTE                              882
                                         V                                                IV
```

FIG. 6

```
                       10         20         30         40         50
H16879         1  TNLHLSVSMD RDTDQALLT- -LLCGK-RFQ NLDSIIYCN RREDTERIAA   50
E. coli RecQ   1  NIRYMMEKF KPLEQLMRY- --VEQ-RGK SGIIYCN SFAKVEQTAA   50

60         70         80         90        100
H16879        51  LLRTCLHAAW VPGSGGGRAPK TTAFAVYHAGM CSREFRRVCR AFMQGQ-LRV  100
E. coli RecQ  51  ADS-KGIS- ---------- ARAVYHAGL ENNVFADVGE KFQRDD-LQI  100

110        120        130        140        150
H16879       101  VVATVAFGMG . . . . . . . . . . . . . . . . . . . . . . . . . . . . . . . . . . . .  150
E. coli RecQ 101  VVATVAFGMG . . . . . . . . . . . . . . . . . . . . . . . . . . . . . . . . . . . .  150
```

HUMAN GENE RECQ4 ENCODING HELICASE

CROSS-REFERENCE TO RELATED APPLICATION

This application is a divisional of U.S. application Ser. No. 09/463,702, filed Jan. 24, 2000, now U.S. Pat. No. 6,335,435, which is a 371 of PCT/JP98/0344 filed July 10, 1998 the disclosure of which is incorporated herein by reference in its entirety, and Japanese Application Serial No. 200387/1997, filed Jul. 25, 1997, the disclosure of which is incorporated herein by reference in its entirety.

TECHNICAL FIELD

The present invention relates to a gene encoding a protein having a helicase activity, a protein encoded by the gene, a method for producing the protein, and use of the gene and the protein.

BACKGROUND ART

DNA helicases are important enzymes that act on various biological reactions involving DNA in living bodies or microbial cells, and there are a number of types of DNA helicases.

The occurrence of a wide variety of DNA helicases is clearly demonsrated by the fact that the reactions involving DNA include a variety of reactions, such as replication and proliferation of cells, development and growth of an individual, and sustainment of life. As the recognized biochemical reactions occurring at the cellular level, there are assumed at least five reactions including replication, repairing, transcription, segregation and recombination of DNAs. DNA helicases are generally known to act to unwind a duplex DNA into single-stranded forms, and the energy required to such an action is considered to be provided by the hydrolysis of ATPs.

Among many types of DNA helicases, RecQ-type DNA helicases have recently been found, which individually have a helicase domain with at least about 40% homology to the helicase domain of *Escherichia coli* (*E. coli*) recQ gene at the amino acid level. The RecQ-type helicases have been focused on due to their involvement in various diseases and aging of humans. For example, Bloom's syndrome is a disease frequently inducible various cancers in younger age, and Werner's syndrome is a genetic disease inducible premature aging and abnormal cancer. It has recently been found that these syndromes are caused by mutation of different genes respectively encoding different human RecQ-type DNA helicases (*Cell*, 83, pp.655–666, 1995; and *Science*, 272, pp.258–262, 1996).

A RecQ-type helicase was originally found in *E. coli* by Nakayama et al. (*Mol. Gen. Genet.*, 195, pp.474–480, 1984). Two kinds of genes encoding proteins having high homology to the helicase have been found in an yeast cell and a human cancer cell, which were designated sgs1 (Gangloff et at., *Mol. Cell. Biol.* 14, pp.8391–8398, 1994) and RecQ1 (Seki et al., *Nuc. Acids Res.*, 22, pp.4566–4573, 1994), respectively.

Known helicases belonging to this family are, in unicellular organisms such as *E. coli* and yeast, only the above-mentioned *E. coli* RecQ helicase and sgs1; and in multi-cellular organisms (i.e., human), Bloom DNA helicase (Ellis et al, *Cell*, 83, pp.655–666, 1995) and Werner DNA helicase (Yu et al., *Science*, 272, pp.258–262, 1996) both responsible for the above-mentioned diseases, and RecQ1 helicase whose involvement in diseases is as yet unknown.

DISCLOSURE OF THE INVENTION

The object of the present invention is to provide a human RecQ4 DNA helicase gene, a protein encoded by the gene, a method for producing the protein, and use of the protein and the gene.

The present inventors assumed if there would be many RecQ family of DNA helicases other than the above three kinds in human. The inventors also assumed that, when genes of such helicases underwent mutation, the genes might induce various diseases as observed in Bloom's syndrome and Werner's syndrome and even be causative genes for refractory diseases of which etiologies have been undetermined yet. The inventors have made intensive and extensive studies for solving the above-mentioned problems. As a result, the inventors have succeeded in the cloning of a novel human RecQ4 DNA helicase gene by so-called RACE method. This success led to the achievement of the invention.

That is, the present invention provides a gene encoding:
(a) a protein comprising an amino acid sequence of SEQ ID NO: 2; or
(b) a protein having deletion, substitution or addition of at least one amino acid residue in the amino acid sequence of SEQ ID NO: 2, which has a helicase activity.

The present invention further provides a gene comprising:
(c) DNA comprising a nucleotide sequence of SEQ ID NO: 1; or
(d) DNA hybridizing to the DNA comprising the nucleotide sequence of SEQ ID NO: 1 under stringent conditions, which encodes a protein having a helicase activity.

The present invention further provides an oligonuleotide probe hybridizing to at least a portion of the gene.

The present invention further provides a recombinant vector containing the gene.

The present invention further provides a transformant containing the recombinant vector.

The present invention further provides a method for producing a protein having a helicase activity, comprising culturing the transformant and then collecting the protein from the resultant culture.

The present invention further provides a recombinant protein of:
(a) a protein comprising an amino acid sequence of SEQ ID NO: 2; or
(b) a protein having deletion, substitution or addition of at least one amino acid residue in the amino acid sequence of SEQ ID NO: 2, which has a helicase activity.

The present invention further provides a mouse- or rat-derived protein having a helicase activity, comprising an amino acid sequence having at least 70% homology to the amino acid sequence of the protein; and a mouse- or rat-derived gene encoding the protein.

The present invention further provides a method for producing a protein having a helicase activity, comprising culturing the transformant and then collecting the protein from the resultant culture.

The present invention further provides a monoclonal or polyclonal antibody specifically reacting with the protein.

The present invention further provides a hybridoma producing the monoclonal antibody, which is prepared by cell fusion of an antibody-producing cell immunized with the protein with a myeloma cell.

The present invention further provides a reagent for detecting a gene encoding helicase, comprising the oligonucleotide probe.

The present invention further provides a kit for diagnosing a disease caused by the genetic abnormality of a gene encoding a protein with a helicase activity, the kit comprising the protein and the monoclonal antibody and/or the polyclonal antibody.

The present invention further provides a transgenic animal having the gene introduced therein in the modified form, the modification being made such that the expression level of the gene is increased or decreased; and a knockout mouse in which the function of the gene has been treated to be lost.

Hereinafter, the present invention is described in detail.

The gene according to the present invention encodes a novel human RecQ4 DNA helicase, and encodes a protein which comprises an amino acid sequence of SEQ ID NO: 2 or a protein which comprises an amino acid sequence having deletion, substitution or addition of at least one amino acid residue in the amino acid sequence of SEQ ID NO: 2 and has a helicase activity.

The protein according to the present invention contains seven helicase motifs of the known RecQ-type DNA helicase, which are well-conserved between *E. coli*, yeast and human at the amino acid level, as shown in FIG. 2. As is clearly demonstrated by the results of the radiation hybrid mapping shown in FIG. 3, it is confirmed that the human RecQ-type DNA helicase gene of the present invention is located on the long arm of human chromosome 8, 8q24.3, as shown in FIG. 4. Genes derived from other species which correspond to the human-derived gene of the present invention can also be cloned by known techniques.

From the results of the multi-tissue northern blot analysis for determining the expression level of the gene of the present invention in different organs (see FIG. 5), it is found that the expression of the gene is observed in all of the tissues examined, and a remarkably intensive expression is particularly observed in thymus and testis.

These results strongly suggest that the gene of the present invention is one of the genes responsible for the maintenance of the fundamental homeostasis of living bodies. Accordingly, the gene is useful for studying on the relation with development and aging of individuals. The elucidation of the expression control of the gene is also useful in the elucidation of the mechanism for maintaining the fundamental homeostasis of living bodies, as well as in the development of novel pharmaceuticals for maintaining the fundamental homeostasis for life.

The gene of the present invention can be identified and obtained by the following procedures, for example.

1. Cloning of Human RecQ-type DNA Helicase Gene

The gene of the present invention (hereinafter, also referred to as "human RecQ4 gene" or "human RecQ-type DNA helicase gene") can be produced by performing RACE method (Rapid Amplification of cDNA Ends; Frohman, M. A. et al., Methods Enzymol. Vol. 218, pp.340–358, 1993) based on the combination of the principles of Long-distance (LD) PCR method and Suppression PCR method.

That is, a DNA fragment comprising a partial sequence of the known human RecQ-type DNA helicase gene and DNA fragments of unknown sequences respectively having the 5' and 3' termini are amplified separately and then linked together, thereby giving the human RecQ-type DNA helicase gene of the present invention in the form of a full-length cDNA. In the present invention, the full-length cDNA may be cloned by, for example, using a commercially available kit such as Marathon™ cDNA Amplification Kit produced by CLONTECH.

At first, a DNA fragment comprising the human-derived known sequence is amplified. The known sequence may be prepared from poly(A)+RNA derived from a human tissue or organ, such as poly(A)+RNA derived from human testis or spleen. The RNA is treated with reverse transcriptase to synthesize cDNA, which is then subjected to RT-PCR to prepare a partial cDNA fragment [FIG. 1 (1)]. The partial cDNA fragment is sequenced. Based on the determined sequence, four kinds of gene-specific primers (GSPs) are designed, which are designated "5'GSP1" and "5'GSP2", and "3'GSP1" and "3'GSP2", respectively. These GSPs are required for the amplification of DNA fragments of unknown sequences to be located upstream to the 5' region and downstream to the 3' region of the partial cDNA sequence, respectively. The GSPs have nucleotide sequences suitably selected among the sequence of the partial cDNA, and may be synthesized chemically. In the present invention, the GSPs used for the amplification of the fragment of unknown sequence to be located upstream to the 5' region of the partial cDNA are "5'GSP1" and "5'GSP2", and those used for the amplification of the fragment of unknown sequence to be located downstream to the 3' region of the partial cDNA are "3'GSP1" and "3'GSP2", as shown in a open box of FIG. 1(1).

Next, the DNA fragments to be located upstream to the 5' region and downstream to the 3' region of the partial cDNA are separately amplified [FIG. 1 (2)]. As templates for the amplification, commercially available cDNAs derived from human testis, spleen or the like may be used, such as cDNA Ready™ made by CLONTECH. Although the sequences of the template DNA fragments are unknown, each of them has an adapter sequence attached to the terminus. Amplification reaction (LD PCR) of the cDNA fragments of unknown sequences having adapter sequences attached was separately performed two rounds using primers hybridizing to the adapter sequences (hereinafter, simply referred to as "adapter primers (APs)") and the GSPs as primers (FIG. 1(2)). For example, the 5' unknown sequence may be amplified by performing the first PCR using AP1 and 5'GSP1, and then performing the second PCR using the fragment produced by the first PCR as a template and primers (AP2 and 5'GSP2) hybridizing to the inner regions relative to the regions for AP1 and 5'GSP1, respectively (i.e., nested PCR). The 3' unknown sequence can also be amplified in the same manner as for the 5' unknown sequence using 3'GSP1 and 3'GSP2.

In the present invention, the DNA fragment to be located upstream to the known fragment is referred to as a "5'-RACE product", and the DNA fragment to be located downstream to the known fragment is referred to as a "3'-RACE product". Since each AP has the same sequence as the protrusion sequence of the corresponding adapter, it cannot anneal to the adapter and the extension reaction in the first amplification only starts from the gene-specific primer (GSP) (this is called "Suppression PCR").

The nucleotide sequence of the resultant cDNA may be determined by a PCR-based method as described by Hattori et al. (Electrophoresis 13, pp.560–565, 1992). That is, the reaction is performed using PRISM sequencing kit including a fluorescent dye deoxyterminetor produced by Perkin Elmer, the nucleotide sequence is read out using an autosequencer manufactured by Applied Biosystem (Model ABI 373) and the data is analyzed by the computer (e.g., Macintosh computer) attached to the autosequencer.

The nucleotide sequences of the known partial DNA sequence, the 5'-RACE product and the 3'-RACE product are assembled together, thereby giving a nucleotide sequence of a full-length cDNA. That is, the overlapped portions between the sequences are linked to give a nucleotide sequence having the 5' and 3' terminal regions (FIG. 1).

The nucleotide sequence of the gene of the present invention and the amino acid sequence of the protein encoded by the gene are shown in SEQ ID NOs: 1 and 2, respectively. However, the gene or protein may have mutation such as deletion, substitution, addition or insertion in the nucleotide or amino acid sequence, provided that the protein comprising the amino acid sequence of SEQ ID NO: 2 exerts a helicase activity. For example, the amino acid sequence of SEQ ID NO: 2 may have deletion of at least one, preferably 1–10, more preferably 1–5 of amino acid residues, addition of at least one, preferably 1–10, more preferably 1–5 of amino acid residues, or substitution of at least one, preferably 1–10, more preferably 1–5 of amino acid residues by other amino acid residues. Accordingly, a protein having deletion of the first methionine (Met) in the amino acid sequence of SEQ ID NO: 2 is also encompassed in the proteins having these amino acid alternations of the present invention. In addition to the nucleotide sequences encoding the amino acids contained in the protein of the present invention, the gene of the present invention also encompasses a degenerate variant of the gene encoding the same protein which is only different at a degenerated genetic codon.

In addition to the gene comprising DNA comprising a nucleotide sequence of SEQ ID NO: 1, the gene of the present invention also encompasses a gene comprising DNA hybridizing to such DNA under stringent conditions and encoding a protein with a helicase activity. As used herein, the term "stringent conditions" refer to conditions such as those at a sodium concentration of 15–60 mM, preferably 15–30 mM, and a temperature of 55–70° C., preferably 60–70° C.

The above-mentioned mutation may be introduced by any one of the known techniques. For this purpose, for example, a commercially available point mutagenesis kit (e.g., "TAKARA LA PCR in vitro Mutagenesis Kit" produced by Takara Shuzo Co., Ltd.) may be employed.

The protein of the present invention also encompasses a protein comprising an amino acid sequence with at least 70% homology to the amino acid sequence of the above-mentioned protein. The gene encoding such a protein is also encompassed in the gene of the present invention. Examples of such protein and gene include those derived from a mouse and rat.

Once the nucleotide sequence is determined, the desired gene can be prepared by PCR using the primers (e.g., those as shown in SEQ ID NOs: 35 and 36) that are synthesized chemically or based on the determined nucleotide sequence or by hybridization using, as a probe, a DNA fragment having the determined nucleotide sequence.

2. Preparation of Recombinant Vector and Transformant

The recombinant vector of the present invention can be prepared by integrating the gene into a suitable vector. The transformant of the present invention can be prepared by introducing the recombinant vector DNA into a host compatible with a vector which is used for the preparation of the recombinant vector.

The gene is introduced in the purified form into a restriction site or a multi-cloning site of a suitable vector to give a recombinant vector, which recombinant vector is then used to transform a host cell.

The vector DNA into which the DNA fragment is introduced is not particularly limited, and any one may be used provided that it can be replicated in the host cell, such as plasmid DNA, phage DNA and the like. Examples of the plasmid DNA include plasmid pUC118 (Takara Shuzo Co., Ltd.), pUC119 (Takara Shuzo Co., Ltd.), pBluescript SK+ (Stratagene) and pGEM-T (Promega). Examples of the phage DNA include M13mp18 and M13mp19.

The host is not particularly limited provided that it can express the gene of interest, and may be either a eukaryotic or prokaryotic cell. Examples of the host include bacteria (e.g., *E. coli, Bacillus subtilis*), yeast (e.g., *Saccharomyces cerevisiae*), and animal cells (e.g., COS cell, CHO cell).

When a bacterium such as *E. coli* is used as the host, it is preferable that the recombinant vector of the present invention be capable of autonomous replication and, at the same time, have a constitution comprising a promoter, the DNA of the present invention and a transcription termination sequence. For example, *E. coli* may be XL1-Blue (Stratagene) or JM10 (Takara Shuzo Co., Ltd.) and the expression vector may be pBTrp2. The promoter may be of any type provided that it can be expressed in a host (e.g., *E. coli*). Examples of such a promoter include trp promoter, lac promoter, PL promoter and PR promoter which are derived from *E. coli* and phages.

In the present invention, the transformation can be performed by, for example, the method by Hanahan (Techniques for Transformation of *E. coli* In DNA Cloning, vol.1, Glover, D. M. ed., pp.109–136, IRL Press, 1985).

When yeast is used as the host, the expression vector may be YEp13 or YCp50, and the promoter may be gal 1 promoter or gal 10 promoter. The introduction of the recombinant vector into the yeast may be performed by electroporation method (Methods. Enzymol., 194, pp.182–187, 1990), spheroplast method (Proc. Natl. Acad. Sci. USA, 84, pp.1929–1933, 1978), lithium acetate method (J. Bacteriol., 153, 163–168, 1983), or the like.

When an animal cell is used as the host, the expression vector may be pcDNAI and pcDNAI/Amp (Invitrogen). The introduction of the recombinant vector into the animal cell may be performed by electroporation method, calcium phosphate precipitation method or the like.

For example, when a plasmid DNA is used as a vector DNA and an EcoRI DNA fragment is inserted thereinto, the plasmid DNA may be previously digested with a restriction enzyme EcoRI (NEB). The digested vector DNA may be mixed with the DNA fragment of interest, and then T4 DNA ligase (Takara Shuzo Co., Ltd.), for example, may be reacted with the mixture, thereby giving a recombinant vector.

The screening of the transformant strain may be performed by colony hybridization using, as a probe, a DNA fragment containing a portion of the gene of interest, or by PCR method using a 5' primer (FP; forward primer) synthesized based on the nucleotide sequence of the gene of interest and a 3' primer (RP; reverse primer) synthesized based on the nucleotide sequence of DNA complementary to the gene of interest, and selecting colonies containing the gene of interest.

3. Production of Protein (Polypeptide) Encoded by Human RecQ4 Gene

The transformant containing the recombinant vector prepared as mentioned above is cultured to produce the protein of the present invention. The culture method may be a conventional solid culture method. However, a liquid culture method is preferably employed for this purpose.

The culture medium used for culturing the transformant may be, for example, one comprising at least one nitrogen source (e.g., yeast extract, peptone, meat extract), which is supplemented with at least one inorganic salt (e.g., dipostassium hydrogenphosphate, magnesium sulfate, iron(II) chloride) and optionally other additive(s) (e.g., a carbohydrate source, an antibiotic, a vitamin) in an appropriate manner. If necessary, IPTG or the like may also be added to the culture medium to induce the expression of the gene. The culture medium is initially adjusted to pH 7.2–7.4, and the culture is usually performed at 36–38° C., preferably about 37° C., for 14–20 hours by aerated spinner culture method, shaking culture method or the like.

After the culture is completed, the protein of the present invention may be collected from the culture by a conventional protein purification method as follows.

The cells are disrupted by lytic treatment with an enzyme (e.g., lysozyme), ultrasonic disruption treatment, mechanical disruption treatment or the like, thereby releasing the protein encoded by the gene of the present invention from the cells. Then, insoluble matters are removed from the solution by filtration, centrifugation or the like to give a crude protein solution.

The protein may be purified from the crude protein solution by a conventional protein purification method. As such a method, for example, salting out with ammonium sulfate, ion exchange chromatography, hydrophobic chromatography, gel filtration chromatography, affinity chromatography, electrophoresis or the like may be employed singly or in combination.

4. Production of Monoclonal Antibody

The monoclonal antibody specific to the protein encoded by human RecQ4 gene of the present invention may be produced as follows.

(1) Preparation of Antigen

The protein prepared as described in Section 3 above is dissolved in a buffer solution, and an adjuvant is then added thereto. As such an adjuvant, commercially available Freund's complete or incomplete adjuvant or the like may be used singly or in the mixed form.

(2) Immunization and Isolation of Antibody-producing Cells

The immunogen prepared as described above is administered to a mammalian animal (e.g., rat, mouse). A single dose of the antigen used for the immunization may be 10–500 μg per animal. The animal may be immunized by injecting the antigen intravenously, subcutaneously or intraperioneally. The interval of the immunization is not particularly limited, and the immunization may be performed at intervals of several days to several weeks, preferably 1–3 weeks, for 2–5 times, preferably 3–4 times. Two to seven days, preferably four to five days, after the final immunization, antibody-producing cells are isolated. Such antibody-producing cells may be spleen cells, lymph node cells, peripheral blood cells, and preferably spleen cells or localized lymph node cells.

(3) Cell Fusion

The myeloma cells used for cell fusion with the antibody-producing cells may be of a usually commonly available established cell line of an animal (e.g., mouse). The cell line used is preferably one having drug selectivity, and incapable of surviving in a selective medium (HAT medium; comprising hypoxantine, aminopterin and thymidine) in its non-fused form but capable of surviving in such a selective medium only in its fused form with an antibody-producing cell. Specific examples of the myeloma cell include mouse myeloma cell line such as P3U-1 (Dainippon Pharmaceutical Co., Ltd.) and P3×63Ag8.653 The myeloma cells are then fused with the antibody-producing cells. The cell fusion may be performed by mixing the antibody-producing cells with the myeloma cells at a ratio of 100–500 cells of the antibody-producing cells per 1 myeloma cell, for example, by mixing equivalent volumes of a culture medium containing $10^8$ cells/ml of the antibody-producing cells and a culture medium containing $2 \times 10^5$ cells/ml of the myeloma cells, and the mixture is then subjected to fusion reaction in the presence of a fusion promoting agent. For promoting the cell fusion, polyethylene glycol with a mean molecular weight of 1,500 daltons or the like may be used. Alternatively, a commercially available cell fusion apparatus utilizing electrical stimulation (e.g., electroporation) may be employed to cause the cell fusion of the antibody-producing cells with the myeloma cells.

(4) Screening and Cloning of Hybridomas

The desired hybridomas are screened from the cells after the cell fusion treatment. The screening may be performed by appropriately diluting the cell suspension with RPMI-1640 medium containing fetal bovine serum or the like, inoculating the resultant dilution solution into each well of a microtiter plate in an amount of about 5–10 cells/well, adding a selective medium to each well, and then incubating the plate while appropriately replacing the selective medium in the wells by a fresh one. The desired hybridomas can be obtained as the cells grown about 14 days after the culture is started. The culture supernatant of the grown hybridomas is then screened for the presence of the antibodies of interest. The screening may be performed by a conventional method, and the method is not particularly limited. For example, a portion of the hybridoma-containing culture supernatant may be removed from the individual wells and subjected to screening by enzyme immunoassay (EIA), radio immunoassay (RIA) or the like.

The cloning of the fused cells is then performed by a limiting dilution method or the like to ultimately establish hybridomas which produce monoclonal antibodies.

(5) Collection of Monoclonal Antibodies

As the method for collecting monoclonal antibodies from the above-established hybridomas, a conventional cell culture method or ascites fluid production method may be employed. In the case of a cell culture method, the hybridomas are cultured in a culture medium for animal cells, such as RPMI-1640 medium containing 10% fetal bovine serum, MEM medium or a serum-free medium, under conventional culture conditions (e.g., 37° C., 5% $CO_2$) for 10–14 days, and the antibodies can be obtained from the culture supernatant. In the case of an ascites fluid production method, the hybridomas (about $5 \times 10^6$ cells) are administered intraperitoneally to an animal of the same species as that of the mammal from which the myeloma cells are derived, thereby causing to grow the hybridomas in a large scale. One to two weeks later, the ascites fluid or serum is collected from the animal. In these antibody-collecting methods, if it is required to purify the antibodies, a known method such as salting out with ammonium sulfate, ion exchange chromatography, affinity chromatography or gel chromatography may be employed singly or in combination.

5. Production of Polyclonal Antibodies (1) Preparation of Antigen

The protein prepared as described in Section 3 above is dissolved in a buffer solution, and then an adjuvant is added thereto. Such an adjuvant may be commercially available Freund's complete or incomplete adjuvant.

(2) Immunization

The animal used for the immunization may be a rabbit, guinea pig, goat, sheep or the like. In the case of a rabbit, for example, the protein is injected subcutaneously to the foot paw usually at a dose of 100–500 μg together with Freund's complete adjuvant. Two weeks later, the same dose of the antigen mixed with Freund's incomplete adjuvant is injected intramuscularly. Additional two weeks later, the intramuscular injection is repeated. One week after the final immunization, a portion of the blood was collected from the ear and determined for the antibody titer by EIA method or the like. When the antibody titer reaches the desired value, the whole blood was collected. However, if the antibody titer is low, the immunization is repeated until the antibody titer reaches the desired value. The antibodies are then purified from the serum by ammonium sulfate fractionation as mentioned in the above-described relevant section for the purification of the monoclonal antibodies.

6. Reagent for Detecting Human RecQ4 Gene and the Protein Encoding the Gene

Human RecQ4 gene has high degree of homology to the causative genes of Bloom's syndrome and Werner's syndrome which cause chromosomal instability and induce high frequency carcinogenesis and progeria (FIG. 2), and the high expression of the gene is observed in various human tissues (FIG. 5). Therefore, it can be concluded that the gene is one of genes encoding DNA helicases responsible for the maintenance of the fundamental homeostasis of a living body. Accordingly, the elucidation of the expression control of the gene may be useful for the elucidation of the mechanism of the homeostasis maintenance of a living body, useful for the development of novel drugs for maintaining the fundamental homeostasis of a living body, and useful in the study on the elucidation of the relation with aging. The reagent of the present invention is useful for the detection and diagnosis of diseases cause by the abnormality in genes encoding proteins having helicase activity, including, but not limited to, Bloom's syndrome and Werner's syndrome.

When the gene of the present invention is used as a reagent, the hybridization may be performed using an oligonucleotide containing at least a portion of the cloned human RecQ4 gene as a probe, and the detection may be performed by Southern or Northern blotting method. As such an oligonucleotide probe, a DNA probe, an RNA probe or the like may be used.

When the polyclonal or monoclonal antibody to the protein encoded by the gene of the present invention is used as a detection reagent, the detection may be performed by EIA, RIA or Western blotting analysis.

7. Transgenic Animals Having the Gene Introduced therein in the Modified Form such that the Expression Level of the Gene Increases or Decreases In the present invention, the gene can be artificially modified to increase or decrease the expression level thereof compared to the normal level by causing a mutagenesis (e.g., deletion, substitution, addition, insertion) at a portion of the several sites important for controlling the expression of the gene (e.g., enhancer, promoter, intron).

The mutagenesis may be performed by any one of the known methods. For example, a commercially available point mutagenesis kit (e.g., TAKARA LA PCR in vitro Mutagenesis kit produced by Takara Shuzo Co., Ltd.) may be used. The transgenic animal includes, for example, a transgenic mouse and a transgenic rat. The vector containing the mutagenized gene may be a vector capable of overexpression of RecQ4 genes from different animal species or a vector capable of suppressing the expression of such RecQ4 genes. In either case, a drug-resistance gene (e.g., a neomycin-resistance gene) is ligated to the gene for the positive selection.

The introduction of the gene may be performed by directly injecting the DNA into fertilized eggs. However, it is preferable to utilize embryonic stem (ES) cells to achieve the efficient introduction of the gene, because ES cells have such an advantage that they can be cultured and they can develop mice or the like therefrom. The ES cells may be TT2 cells (Shin-ichi AIZAWA, "Gene Targeting", 1995, Yodosha). For example, the vector DNA containing murine RecQ4 gene is introduced into ES cells by electroporation, and positive clones are selected with neomycin, thereby giving mutant ES cells of interest. The mutant ES cells are then injected to blastcysts or 8-celled embryos through a capillary or the like. The blastcysts or 8-celled embryos may be implanted direct into the oviduct of a foster parent. Alternatively, they may be developed to the blastocyst stage and then implanted to the uterus of a foster parent. Among the progenies bred from the foster parent, chimeras are selected. The animals with high contribution to the chimeras have high possibility of animals of the germ line of the chimeras. Whether an animal is a chimera of the germ line of this chimera can be determined by mating the animal with a normal (i.e., wild-type) one. The mating of the germ line of the chimera with a normal one results in the production of heterozygotes, and the mating between the heterozugotes results in the production of homozygotes.

8. Knockout Mouse

The knockout mouse of the present invention is prepared by treating a mouse so that the function of murine RecQ4 gene is lost. The method for the treatment is described below.

A genomic DNA containing murine RecQ4 gene is prepared from the genomic DNA from a murine ES cell by PCR or from a genomic library. A neo-resistance gene is introduced into any one of the exons of the genomic DNA to construct a vector. This procedure results in the disruption of the function of the exon. At the same time, a thymidine kinase (tk) gene or a diphtheria toxin (DT) gene is also introduced into the vector for the negative selection. The vector DNA is introduced into ES cells by electroporation. The cells are then cultured in the presence of neomycin for the selection of positive clones or a nucleic acid analogue FIAU (fluoroiodoadenosyluracil) or diphtheria toxin for the selection of negative clones. By this procedure, diphtheria toxin-sensitive cells in which non-homologous recombination occurs and G418-sensitive cells in which no recombination occurs are removed out, and only cells in which homologous recombination occurs are remained. In the cells in which homologous recombination occurs, the gene containing the disrupted exon undergoes knockout. The resulted cells are injected into murine blastcysts or 8-celled embryos. Thereafter, the same procedures as for the preparation of the transgenic animal are performed to produce knockout mice.

BRIEF DESCRIPTION OF THE DRAWINGS

FIG. 2 illustrates the comparison in amino acid sequence homology between the protein encoded by human RecQ4 gene (SEQ ID NO: 37) and proteins (*E. coli* RecQ (SEQ ID NO: 38), yeast SES1 (SEQ ID NO: 39), RecQ, (SEQ ID NO: 40), Bloom (SEQ ID NO: 41), and Werner (SEQ ID NO: 42) derived from other genes.

FIG. 6 illustrates the comparison in amino acid sequence homology between the protein encoded by EST-DNA ACC. H16879 (SEQ ID NO: 43)and a protein derived from *E. coli* (SEQ ID NO: 44).

BEST MODE FOR CARRYING OUT THE INVENTION

Figure 1:
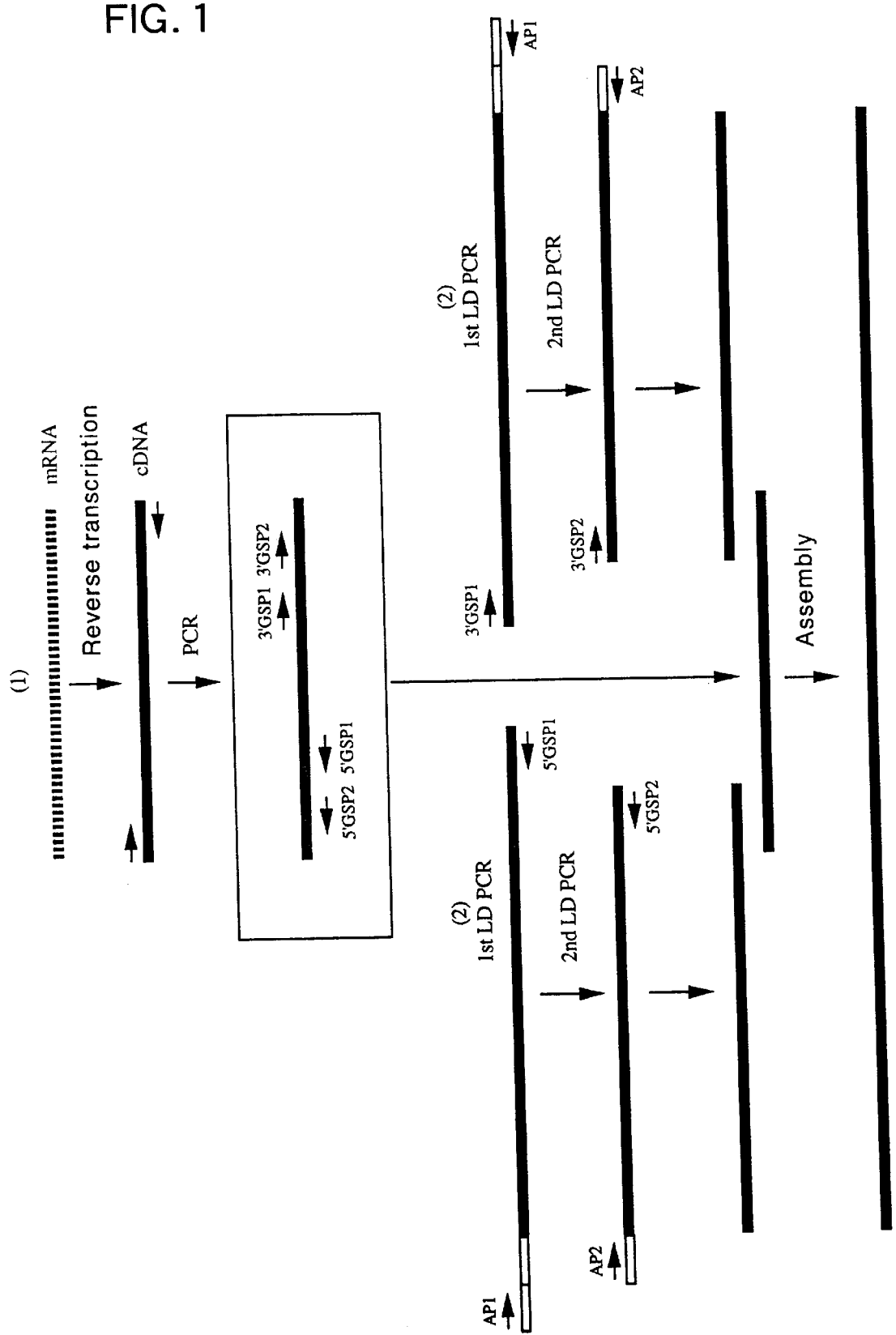
FIG. 1 illustrates the procedures for cloning the gene according to the present invention.
Figure 3:
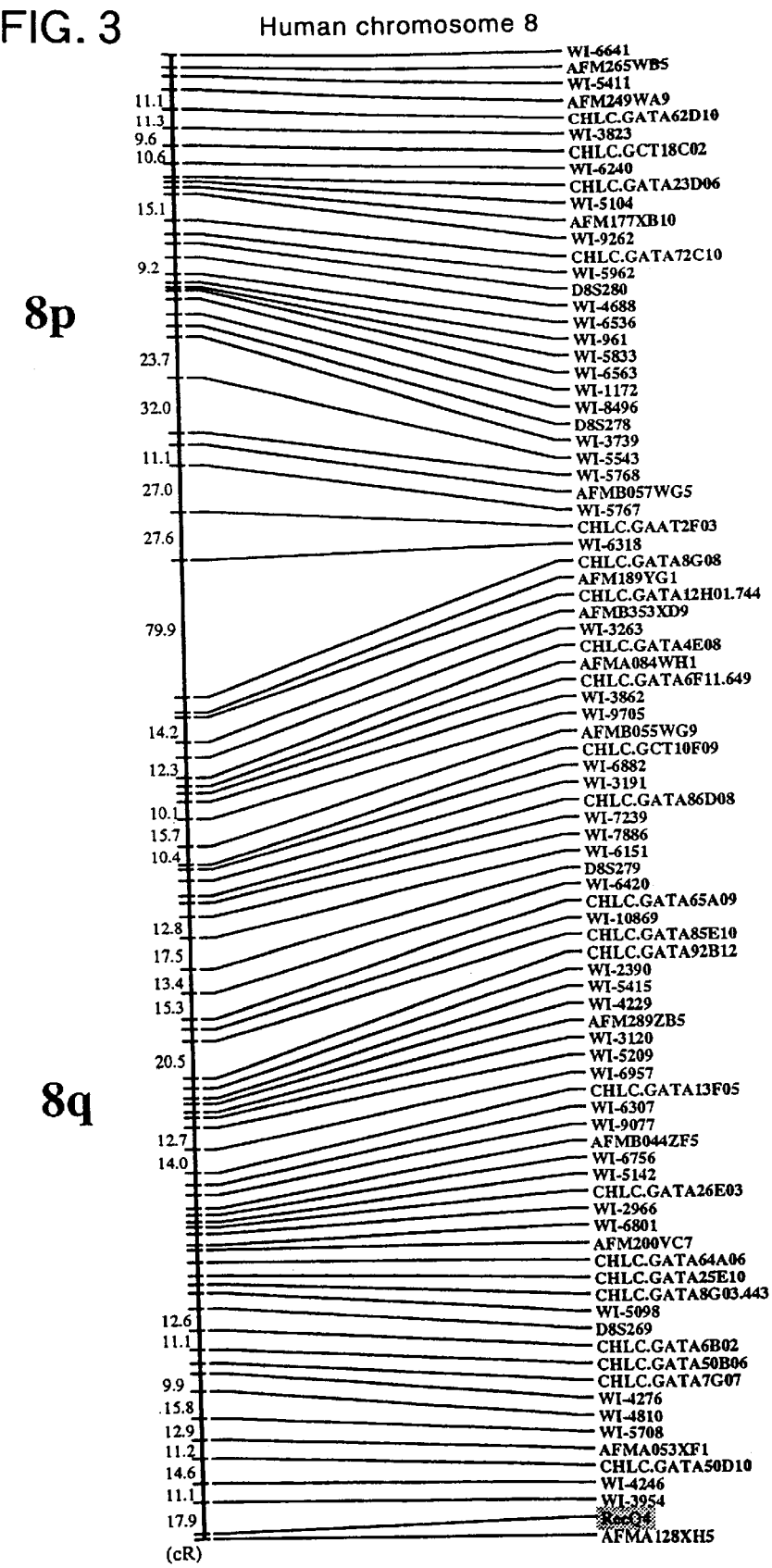
FIG. 3 illustrates the radiation mapping analysis indicating the location of human RecQ4 gene on human chromosome 8.
Figure 4:
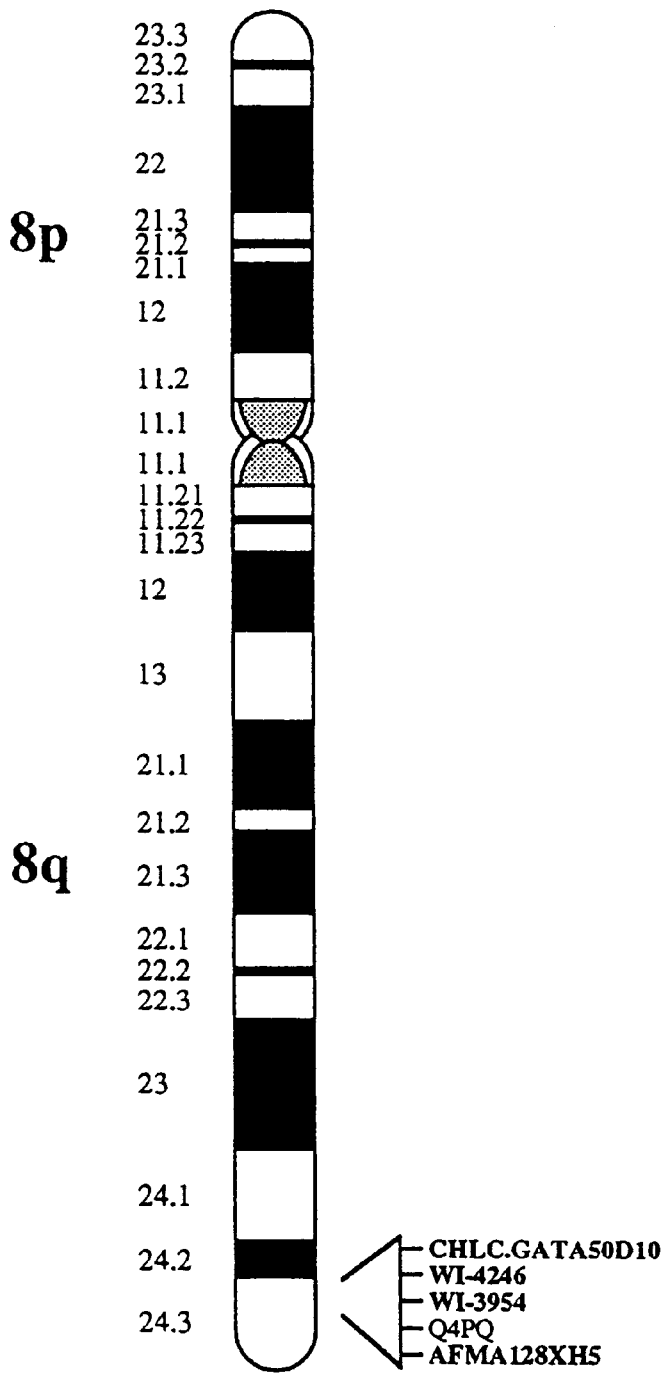
FIG. 4 illustrates human chromosome 8.

Hereinafter, the present invention is illustrated in more detail, However, the following examples are intended to illustrate but not admitted to limit the technical scope of the invention.

EXAMPLE 1

Cloning of Full-length Human RecQ4 cDNA (1) Identification of a cDNA Fragment having Homology to E. coli RecQ4 DNA Helicase Before the cloning of the DNA of the present invention, the dbest database was searched for a cDNA sequence having homology to E. coli RecQ helicase. As a result, there were found more than ten kinds of EST (Expressed Sequence Tag) DNAs including EST-DNA ACC. H 16879 (i.e., DNA encoding the amino acid sequence of H16879 shown in FIG. 6). In consideration of the nucleotide sequence homology of these ESTs to the EST-DNAs derived from organisms other than human (e.g., E. coli, yeast, threadworms) or with the genes of the known human-derived Blooms's disease helicase, Werner's disease helicase and RecQ1 helicase, those having high nucleotide sequence homology to such genes were omitted from the above-found ESTs.

(2) Identification of EST-DNA ACC.H16879 as the Gene Expressed in Human Tissues

Next, a series of preliminary experiments were performed to identify the sequence of EST-DNA ACC.H16879 as the gene truly expressed in human tissues. That is, a sense primer (SEQ ID NO: 3) and an antisense primer (SEQ ID NO: 4) for PCR (Polymerase Chain Reaction) were provided based on the nucleotide sequence contained in the EST-DNA fragment. On the other hand, cDNA was prepared from mRNA derived from human testis by reverse transcription reaction. PCR was performed using the above-prepared primers to examine for the presence of the EST-DNA in the human testis-derived cDNA.

RT-PCR was performed as described in (3-i) below. As a result, a predicted PCR product of about 320 bp could be detected from the sequence of EST-DNA ACC.H16879.

The confirmation of the presence or absence of the EST-DNA by PCR could also be performed by integrating the DNA fragment amplified by PCR into a plasmid DNA of E. coli, cloning the DNA fragment, and then analyzing the nucleotide sequence of the resultant plasmid clone DNA. In this manner, it was confirmed that EST-DNA ACC.H16879 was a portion of the novel helicase gene. [As for the procedures, see (3-ii) and (3-iii) below.]

(3) Cloning of a Partial cDNA Fragment of Human RecQ4 Gene by RT-PCR (3-i) Preparation of cDNA by Reverse Transcription and Amplification A reaction solution comprising human testis-derived poly (A)+RNA (CLONTECH) (about 1 µg), dithiothreitol, dNTPs (dATP, dCTP, dGTP and dTTP), a buffer for a reverse transcriptase, and a reverse transcriptase Super Sucript II, was allowed to react at 42° C. for 30 minutes, and then subjected to RNase treatment, thereby preparing cDNA. The cDNA was used as a template for the subsequent PCR.

In the PCR, TAKARA Taq (Takara Shuzo Co., Ltd.) and a buffer attached thereto were used. If not otherwise stated, the "Taq DNA polymerase" and "PCR buffer" used hereinbelow refer to TAKARA Taq and the buffer attached thereto, respectively. PCR was performed in a mixed reaction solution (25 µl) comprising a solution containing 1×PCR buffer, 0.2 mM dNTPs, 0.4 µM RecQ4 primers (SEQ ID NOs: 3 and 4) and 0.625 unit Taq DNA polymerase with an appropriate amount of the human testis-derived cDNA.

The reaction solution was allowed to react, starting with at 94° C. for 5 min., and then at a program of 94° C. for 30 sec.; 55° C. for 30 sec.; and 72° C. for 1 min. for 35 cycles. The resultant reaction solution was additionally allowed to react at 72° C. for 5 min.

(3-ii) Subcloning of PT-PCR Product for Sequencing

A solution containing the PT-PCR product obtained in (3-i) above, T4 DNA ligase (Takara Shuzo Co., Ltd.), buffer (Takara Shuzo Co., Ltd.) and pGEM-T vector (Promega) was allowed to react at 15° C. for 3 hours, thereby causing the integration of the PT-PCR product fragment into pGEM-T vector. E. coli JM109 was transformed with the vector, and the resultant E. coli transformant was plated on LB bactoagar plate containing X-gal, IPTG and ampicillin (final concentration: 50 µg/ml) and incubated at 37° C. for 12 hours. White E. coli colonies that appeared on the plate were subjected to shaking culture in LB medium containing ampicillin (final concentration: 50 µg/ml) at 37° C. for 16 hours or more, and plasmid DNA was prepared using a robot (PI-100Σ manufactured by Kurabo).

The resultant plasmid DNA was dissolved in dH₂O (100 µl) containing 10 µg/ml of RNase for use as a sample for the subsequent DNA sequencing.

(3-iii) Sequencing

PCR was performed using the plasmid DNA prepared in (3-ii) above as a template in a reaction system containing non-labeled primers, four kinds of fluorescent labeled nucleotide-5'-triphosphate and Taq polymerase. The composition of the reaction solution is as follows.

| | |
|---|---|
| Thermal Ready reaction mixture | 8.0 µl |
| Template DNA | 3.0 µl |
| Primer (3.2 pmol/µl) | 1.0 µl |
| dH₂O | 8.0 µl |
| Total | 20 µl |

In this PCR, primers shown in SEQ ID NOs: 5–19 were used as the primers for the sequencing.

PCR was performed at a program of 96° C. for 30 sec. (denaturation); 55° C. for 15 sec. (annealing); and 60° C. for 4 min. (elongation), for 25 cycles. By this reaction, DNA fragments each having a randomly inserted fluorescent dye were synthesized. The nucleotide sequences of these DNA fragments were individually analyzed using a sequencer. Thus, finally, a continuous nucleotide sequence could be determined. The analysis of the PCR products was performed using an automated DNA sequencer, model ABI 373 manufactured by Applied Biosystem. The nucleotide sequence of the partial human RecQ4 cDNA is shown in SEQ ID NO: 31.

(4) Cloning of the 5' and 3' Regions of Human RecQ4 Gene using Marathon cDNA Amplification Kit Based on the nucleotide sequence of the partial human RecQ4 cDNA obtained in (3) above, cloning of the 5' and 3' regions of the human RecQ4 gene was performed using Marthon cDNA Amplification kit (CLONTECH). At first, to amplify the 5' RACE product, the first round RCR was performed using Marathon Ready testis-derived cDNA as a template and primer AP1 (SEQ ID NO: 20) specific to the adapter sequence and primer 5'GSP1 (SEQ ID NO: 22) specific to the partial RecQ4 cDNA fragment. The composition of the reaction solution used for this PCR is as follows.

| | |
|---|---|
| Template | 5 μl |
| Primers (10 mM) | 1 μl × 2 |
| 10x Klen Taq reaction buffer | 5 μl |
| 2.5 mM dNTPs mix | 4 μl |
| Klen Taq (CLONTECH) | 1 μl |
| dH₂O | 33 μl |
| Total | 50 μl |

The PCR was performed, starting with denaturation step at 94° C. for 1 min., at a program of 94° C. for 30 sec. (denaturation) and 72° C. for 4 min. (annealing and elongation) for 5 cycles; then at a program of 94° C. for 30 sec. (denaturation) and 70° C. for 4 min. (annealing and elongation) for 5 cycles; and then at a program of 94° C. for 30 sec. (denaturation) and 68° C. for 4 min. (annealing and elongation) for 25 cycles.

Using the resultant reaction solution in a diluted form as a template, the second round PCR was performed using the further inner primer pairs, AP2 (SEQ ID NO: 21) and 5'GSP2 (SEQ ID NO: 23), thereby giving a 5' RACE product of about 2 kbp. The same procedures were repeated using primer pairs, 3'GSP1 (SEQ ID NO: 24) and 3'GSP2 (SEQ ID NO: 25), thereby giving a 3' RACE product of about 1.5 kbp. These products were separately subcloned into pGEM-T vector, and the full-length sequences of the 5' and 3' RACE products were determined [as for the method, see (3-ii) and (3-iii) above].

The nucleotide sequences of the obtained 5' and 3' RACE products of human RecQ4 gene are shown in SEQ ID NOs: 32 and 33, respectively.

(5) Determination of the Transcription Origin for RecQ4 Gene

As a result of the analysis of the nucleotide sequence of the 5' RACE product, the first methionine of the predicted protein encoded by RecQ4 gene was not found in the 5' RACE product, and it was assumed that the first methionine would be located further upstream to the 5' RACE product. Then, the transcription origin of the gene was determined as follows.

A 5' region containing the transcription origin for RecQ4 gene was determined by oligo-capping method. Human testis-derived mRNA was treated with calf small intestine-derived alkaline phosphatase (CIAP) (Takara Shuzo Co., Ltd.) to dephosphorylate the mRNA. The composition of the reaction solution used is as follows.

| | |
|---|---|
| Human testis-derived mRNA | 10 μg |
| 10x CIAP buffer (Takara Shuzo Co., Ltd.) | 10 μl |
| RNasin (Promega) | 4 μl |
| CIAP (Takara Shuzo Co., Ltd.) | 1 μl |
| dH₂O | to 100 μl |

The reaction was performed at 37° C. for 30 min. Subsequently, the dephosphorylated mRNA was treated with tobacco acid pyrophosphatase (TAP) (Nippon Gene) to remove the 5' CAP structure therefrom. The composition of the reaction solution used is as follows.

| | |
|---|---|
| Dephosphorylated mRNA | 10 μg |
| 10x TAP buffer (Nippon Gene) | 10 μl |
| RNasin (Promega) | 4 μl |

-continued

| | |
|---|---|
| TAP (Nippon Gene, 300 U/μl) | 1 μl |
| dH₂O | to 100 μl |

The reaction was performed at 37° C. for 60 min. Subsequently, the mRNA (TAP-RNA) without CAP structure was ligated with an oligo RNA (SEQ ID NO: 26) of 30 bp as an adapter using T4 RNA ligase (Takara Shuzo Co., Ltd.). The composition of the reaction solution used is as follows.

| | |
|---|---|
| TAP-RNA | 10 μg |
| Oligo RNA (2 μg/μl) | 5 μl |
| 10x ligase buffer (Takara Shuzo Co., Ltd.) | 10 μl |
| 100 mM ATP | 0.5 μl |
| RNasin (Promega) | 4 μl |
| RNA ligase (Takara Shuzo Co., Ltd.) | 5 μl |
| 60% PEG6000 (Nippon Gene) | 42 μl |
| dH₂O | to 100 μl |

The reaction was performed at 18° C. for 16 hours. The resultant reaction product was treated with phenol to remove proteins therefrom and then subjected to ethanol precipitation, thereby giving an oligo-capping RNA. The oligo-capping RNA was dissolved in dH₂O(50 μl). A single stranded cDNA was synthesized using the oligo-capping RNA as a template. The composition of the reaction solution used is as follows.

| | |
|---|---|
| Oligo-capping RNA | 50 μl |
| Random hexamer (20 μM) | 5 μl |
| | 55 μl |

The reaction solution was heated at 70° C. for 10 min. and then chilled on ice, and the following reagents were added thereto.

| | |
|---|---|
| 5x First strand buffer (Gibco) | 20 μl |
| 0.1 M DTT (Gibco) | 10 μl |
| 20 μM dNTPs | 5 μl |
| RNasin (Promega) | 5 μl |
| | 95 μl |

The reaction solution was incubated at 37° C. for 2 min., then Superscript II (Gibco) (5 μl) was added thereto, and the reaction mixture was allowed to react at 37° C. for 30 min. After the reaction was completed, the resultant solution was heated at 95° C. for 10 min, and then dH₂O was added thereto to the total volume of 500 μl, which was served as an oligo-capping cDNA. PCR was performed using the oligo-capping cDNA as a template. The PCR was performed two rounds. Using the first round PCR product as a template, the second round PCR was then performed (i.e., nested PCR). The composition of the reaction solution used for the first round PCR is as follows.

| | |
|---|---|
| Oligo-capping cDNA | 1 μl |
| Sense primer (SEQ ID NO: 27)(20 μM) | 0.5 μl |

-continued

| | |
|---|---|
| Antisense primer (SEQ ID NO: 29)(20 μM) | 0.5 μl |
| 10× PCR buffer | 2.5 μl |
| 2.5 mM dNTPs | 2.0 μl |
| 50% Glycerol | 2.5 μl |
| Taq DNA polymerase | 0.5 μl |
| dH$_2$O | 15.5 μl |
| Total | 25 μl |

The PCR was performed, starting with a denaturation step at 95° C. for 5 min., and then at a program of 94° C. for 30 sec. (denaturation); 60° C. for 30 sec. (annealing); and 72° C. for 1 min. (elongation) for 35 cycles, and ending with 72° C. for 5 min. Using the PCR product as a template, the second round PCR was performed. The reaction solution used for the second PCR was as follows.

| | |
|---|---|
| PCR product | 1 μl |
| Sense primer (SEQ ID NO: 28)(20 μM) | 0.5 μl |
| Antisense primer (SEQ ID NO: 30)(20 μM) | 0.5 μl |
| 10× PCR buffer | 2.5 μl |
| 2.5 mM dNTPs | 2.0 μl |
| 50% Glycerol | 2.5 μl |
| Taq DNA polymerase | 0.5 μl |
| dH$_2$O | 15.5 μl |
| Total | 25 μl |

The second round PCR was performed in the same manner as the first round PCR. Upon the 2% agarose gel electrophoresis, a PCR product of about 400 bp was observed. The PCR product was subcloned into pGEM-T vector and sequenced [as for the methods, see (3-ii) and (3-iii) above]. In the sequencing, a primer pair of SEQ ID NOs: 5 and 6 was used.

The nucleotide sequence of the obtained 5' transcription origin region of human RecQ4 gene is shown in SEQ ID NO: 34.

(6) Construction of Full-length RecQ4 cDNA by Nucleotide Sequence Assembly

Figure 7:
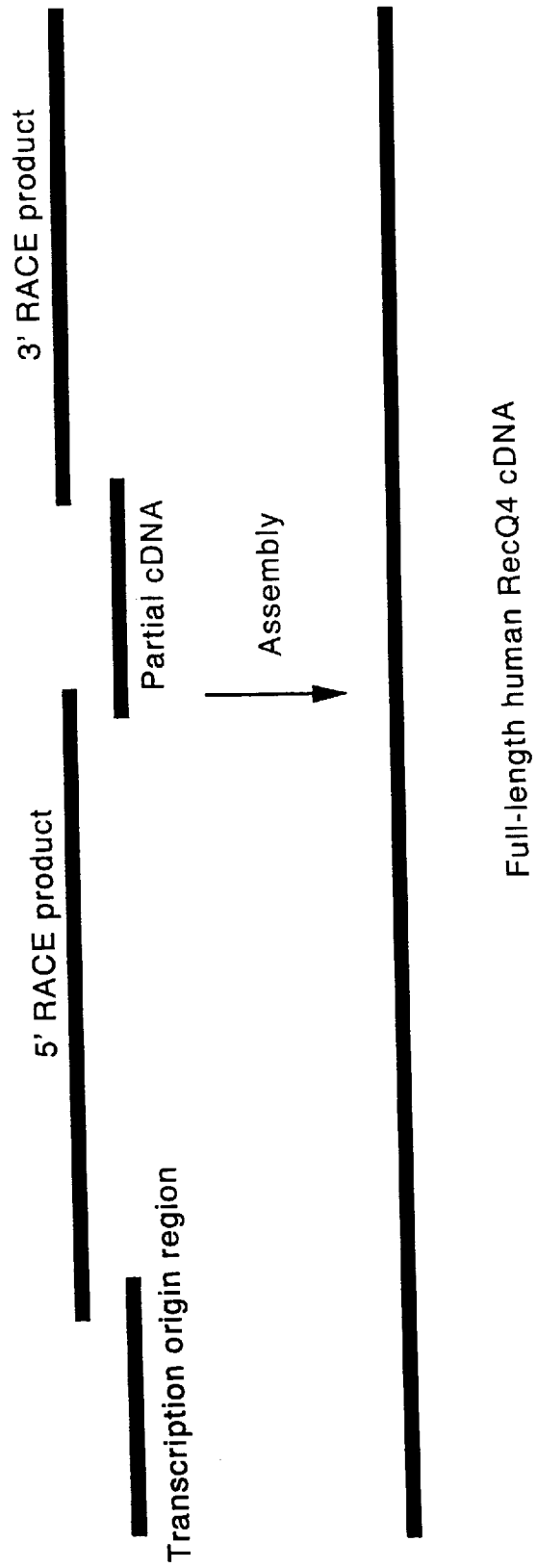
FIG. 7 illustrates the assembly of the gene according to the present invention.

The four nucleotide sequences of human RecQ4 cDNA obtained in (3), (4) and (5) above are shown in SEQ ID NOs: 31–34, respectively. These sequences are overlapped in part one another, and the relative positions of the sequences are as shown in FIG. 7. The transcription origin region, the 5' RACE product, the partial cDNA and the 3' RACE product in FIG. 7 are shown in SEQ ID NOs: 34, 32, 31 and 33, respectively.

These regions were analyzed by computer using DNA-SYS soft wear. The four nucleotide sequences were then ligated together to give a full-length RecQ4 cDNA sequence. The obtained cDNA was composed of 3850 nucleotides in full-length without the 3' poly(A) sequence (see SEQ ID NO: 1). In the cDNA sequence, it was found that the open reading frame (ORF) was composed of 3624 nucleotides and a protein encoded by this sequence consisted of 1208 amino acid residues and had a molecular weight of 133070 daltons. The amino acid sequence of the protein encoded by the gene is shown in SEQ ID NO: 2.

EXAMPLE 2

Analysis of Human RecQ4 Gene by Northern Blotting (1) Northern Blotting Analysis of Human RecQ4 Gene
(1-i) Human Multiple Tissue Northern (MTN-I and -II) Blot In this example, MTN blotting was performed using a commercially available pre-made filter (CLONTECH). The pre-made filter was prepared by electrophoresing poly(A)+ RNAs extracted from 16 kinds of human tissues and organs (2 μg each) on an agarose gel and then blotting the gel on a nylon membrane.

(1-ii) Human RecQ4 cDNA Probe

The open reading frame (a portion of human RecQ4 cDNA; residues 2097–2417 in the nucleotide sequence of SEQ ID NO: 1; 321 bp) was radiolabeled by the method as described in below, which was used as a detection probe for human RecQ4 gene.

(2) Hybridization
(2-i) Pre-hybridization

A filter was immersed in a pre-hybridization buffer (100 ml) in a lunch box-type plastic container, and incubated at 42° C. for 4 hours. This pre-hybridization buffer contained 50% formamide, 5× SSPE, 10× Denhardt's solution, 2% SDS and 100 μg/ml of a denatured salmon spermatic DNA fragment.

(2-ii) Radiolabeling of Human RecQ4 cDNA Probe

Radiolabaling with [α$^{32}$P]-dCTP (NEN, Daiichi Pure Chemicals) was performed using the above-mentioned human RecQ4 cDNA fragment (50 ng) as a template, random hexamer (50 pmol) as a primer and a random primer DNA labeling kit Ver.2 (Takara Shuzo Co., Ltd.).

(2-iii) Hybridization

The pre-hybridization buffer was discarded from the container and a fresh pre-hybridization buffer was added thereto. The container was gently shaken so that no air bubble was formed beneath the filter. The probe radiolabeled with [$^{32}$P]-dCTP was added to the pre-hybridization solution to a specific activity of about 1×10$^6$ cpm/ml, and hybridization was performed at 42° C. for 16 hours.

After the hybridization, the filter was rinsed two times with 2× SSC/0.1% SDS solution (100 ml) at room temperature for 15 min. each, and additionally rinsed two times with 0.2× SSC/0.1% SDS solution (100 ml) at room temperature for 15 min. each.

The filter was dried to such an extent that the filter became slightly moist, and then wrapped in a plastic wrap ("Saran wrap" made by Asahi Chemical Industries, Ltd.) for use in the subsequent autoradiographic analysis using BAS 1500 system (Fujifilm).

(3) Analysis by Fuji BAS 1500 System

The sample was close-exposed to a radiation energy memory type two-dimensional sensor (Imaging Plate; IP) using photostimulable phosphor, like a X-ray film. The IP was excited with a He—Ne laser beam. The luminescence emitted depending on the amount of the exposure light was determined in terms of a digital amount called PSL (Photo Stimulated Luminescence). The determination was performed using BAS 1500 system. The values determined by this system showed a good linearity, and therefore it was found this system could provide for subtraction of background, calculation and comparison of the intensities of radiation in the predetermined regions.

(4) Results of the Tissue-specific Expression of Human RecQ4 mRNA

The [$^{32}$P]-labeled ORF of human RecQ4 cDNA (a portion of human RecQ4 cDNA; nucleotides 2097–2417 in SEQ ID NO: 1; 321 bp) as a probe was hybridized to MTN blot (CLONTECH) containing poly(A)+RNAs derived from various human tissues and organs (2 μg each).

Figure 5:
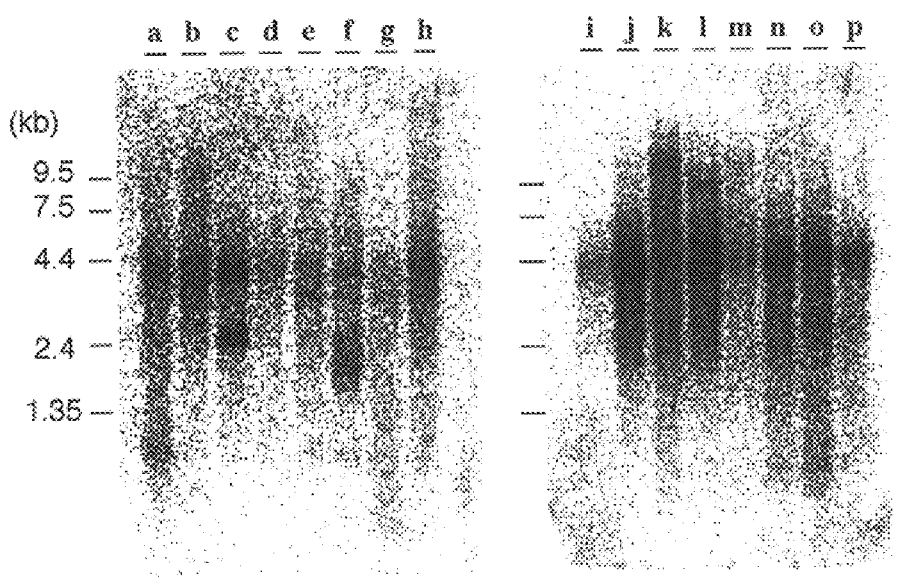
FIG. 5 is a photograph showing the results of the Northern blotting analysis of human RecQ4 gene.

The expression of human RecQ4 mRNA was observed in various organs, and the expression pattern thereof is shown in FIG. 5. That is, human RecQ4 gene was expressed in all tissues, and a remarkably strong expression was particularly observed in thymus and testis. In FIG. 5, the sources from which the poly(A)+RNAs were derived are as follows.

a, heart; b, brain; c, placenta; d, lung; e, liver; f, skeletal muscle; g, kidney; h, pancreas; i, spleen; j, thymus; k, prostate; 1, testis; m, ovary; n, small intestine; o, colon; p, peripheral blood lymphocyte.

INDUSTRIAL APPLICABILITY

According to the present invention, human RecQ4 gene is provided.

The human RecQ4 gene of the present invention is useful for the study on the relation with the maintenance of homeostasis and cell aging in human and the elucidation of the causes of diseases associated with growth and aging, and also useful as a therapeutic for improving and alleviating the conditions of such diseases, a diagnostic probe for detecting and preventing the diseases relating to the other diseases associated with aging, and a reagent for medical, cell biological, immunological, biochemical and molecular biological studies on the development of human individuals.

What is claimed is:

1. An antibody that specifically reacts with a protein consisting of the amino acid sequence of SEQ ID NO:2.

2. The antibody of claim 1, wherein the antibody is monoclonal.

3. The antibody of claim 1, wherein the antibody is polyclonal.

* * * * *

```
                            SEQUENCE LISTING

<160> NUMBER OF SEQ ID NOS: 44

<210> SEQ ID NO 1
<211> LENGTH: 3850
<212> TYPE: DNA
<213> ORGANISM: Homo sapiens
<220> FEATURE:
<221> NAME/KEY: CDS
<222> LOCATION: (85)..(3708)

<400> SEQUENCE: 1
gcattggctg tcggccccg cgacggctgc gcgggagatt cgctggacga tcgcaagcgc      60
ggaggccggg cgggcgcgcg cgcc atg gag cgg ctg cgg gac gtg cgg gag      111
                             Met Glu Arg Leu Arg Asp Val Arg Glu
                             1               5 cgg ctg cag gcg tgg gag cgc gcg ttc cga cgg cag cgc ggg cgg cga     159
Arg Leu Gln Ala Trp Glu Arg Ala Phe Arg Arg Gln Arg Gly Arg Arg
10              15                  20                  25 ccg agc cag gac gac gtg gag gcg gcg ccg gag gag acc cgc gcg ctc     207
Pro Ser Gln Asp Asp Val Glu Ala Ala Pro Glu Glu Thr Arg Ala Leu
                30                  35                  40 tac cgg gag tac cgc act ctg aag cgt acc acg ggc cag gcc ggc ggc     255
Tyr Arg Glu Tyr Arg Thr Leu Lys Arg Thr Thr Gly Gln Ala Gly Gly
            45                  50                  55 ggg ctc cgc agc tcc gag tcg ctc ccc gcg gcg gcc gaa gag gcg cca     303
Gly Leu Arg Ser Ser Glu Ser Leu Pro Ala Ala Ala Glu Glu Ala Pro
        60                  65                  70 gag ccc cgc tgc tgg ggg ccc cat ctg aat cgg gct gcg acc aag agt     351
Glu Pro Arg Cys Trp Gly Pro His Leu Asn Arg Ala Ala Thr Lys Ser
    75                  80                  85 cca cag cct acg cca ggg cgg agc cgc cag ggc tcg gtg ccg gac tac     399
Pro Gln Pro Thr Pro Gly Arg Ser Arg Gln Gly Ser Val Pro Asp Tyr
90                  95                 100                 105 ggg cag cgg ctc aag gcc aat ctg aaa ggc acc ctg cag gcc gga cca     447
Gly Gln Arg Leu Lys Ala Asn Leu Lys Gly Thr Leu Gln Ala Gly Pro
                110                 115                 120 gcc ctg ggc cgc aga ccg tgg cct cta gga aga gcc tca tct aag gca     495
Ala Leu Gly Arg Arg Pro Trp Pro Leu Gly Arg Ala Ser Ser Lys Ala
            125                 130                 135 tcc acc cca aag ccc cca ggt aca ggg cct gtc ccc tcc ttt gca gaa     543
Ser Thr Pro Lys Pro Pro Gly Thr Gly Pro Val Pro Ser Phe Ala Glu
        140                 145                 150 aaa gtc agt gat gag cct cca cag ctc cct gag ccc cag cca agg cca     591
Lys Val Ser Asp Glu Pro Pro Gln Leu Pro Glu Pro Gln Pro Arg Pro
    155                 160                 165 ggc cgg ctc cag cat ctg cag gca tcc ctg agc cag cgg ctg ggc tcc     639
Gly Arg Leu Gln His Leu Gln Ala Ser Leu Ser Gln Arg Leu Gly Ser
170                 175                 180                 185
```

-continued

| | | |
|---|---|---|
| cta gat cct ggc tgg tta cag cga tgt cac agt gag gtc cca gat ttt<br>Leu Asp Pro Gly Trp Leu Gln Arg Cys His Ser Glu Val Pro Asp Phe<br>              190                       195                    200 | 687 |
| ctg ggg gcc ccc aaa gcc tgc agg cct gat cta ggc tca gag gaa tca<br>Leu Gly Ala Pro Lys Ala Cys Arg Pro Asp Leu Gly Ser Glu Glu Ser<br>205                       210                      215 | 735 |
| caa ctt ctg atc cct ggt gag tcg gct gtc ctt ggt cct ggt gct ggc<br>Gln Leu Leu Ile Pro Gly Glu Ser Ala Val Leu Gly Pro Gly Ala Gly<br>     220                   225                    230 | 783 |
| tcc cag ggc cca gag gct tca gcc ttc caa gaa gtc agc atc cgt gtg<br>Ser Gln Gly Pro Glu Ala Ser Ala Phe Gln Glu Val Ser Ile Arg Val<br>235                       240                      245 | 831 |
| ggg agc ccc cag ccc agc agc agt gga ggc gag aag cgg aga tgg aac<br>Gly Ser Pro Gln Pro Ser Ser Ser Gly Gly Glu Lys Arg Arg Trp Asn<br>250                     255                    260                    265 | 879 |
| gag gag ccc tgg gag agc ccc gca cag gtc cag cag gag agc agc caa<br>Glu Glu Pro Trp Glu Ser Pro Ala Gln Val Gln Gln Glu Ser Ser Gln<br>              270                       275                    280 | 927 |
| gct gga ccc cca tcg gag ggg gct ggg gct gta gca gtt gag gaa gac<br>Ala Gly Pro Pro Ser Glu Gly Ala Gly Ala Val Ala Val Glu Glu Asp<br>                   285                       290                    295 | 975 |
| cct cca ggg gaa cct gta cag gca cag cca cct cag ccc tgc agc agc<br>Pro Pro Gly Glu Pro Val Gln Ala Gln Pro Pro Gln Pro Cys Ser Ser<br>300                       305                      310 | 1023 |
| cca tcg aac ccc agg tac cac gga ctc agc ccc tcc agt caa gct agg<br>Pro Ser Asn Pro Arg Tyr His Gly Leu Ser Pro Ser Ser Gln Ala Arg<br>     315                   320                    325 | 1071 |
| gct ggg aag gct gag ggc aca gcc ccc ctg cac atc ttc cct cgg ctg<br>Ala Gly Lys Ala Glu Gly Thr Ala Pro Leu His Ile Phe Pro Arg Leu<br>330                     335                    340                    345 | 1119 |
| gcc cgc cat gac agg ggc aat tac gta cgg ctc aac atg aag cag aaa<br>Ala Arg His Asp Arg Gly Asn Tyr Val Arg Leu Asn Met Lys Gln Lys<br>              350                       355                    360 | 1167 |
| cac tac gtg cgg ggc cgg gca ctc cgt agc agg ctc ctc cgc aag cag<br>His Tyr Val Arg Gly Arg Ala Leu Arg Ser Arg Leu Leu Arg Lys Gln<br>365                       370                      375 | 1215 |
| gca tgg aag cag aag tgg cgg aag aaa ggg gag tgt ttt ggg ggt ggt<br>Ala Trp Lys Gln Lys Trp Arg Lys Lys Gly Glu Cys Phe Gly Gly Gly<br>              380                       385                    390 | 1263 |
| ggt gcc aca gtc aca acc aag gag tct tgt ttc ctg aac gag cag ttc<br>Gly Ala Thr Val Thr Thr Lys Glu Ser Cys Phe Leu Asn Glu Gln Phe<br>395                       400                    405 | 1311 |
| gat cac tgg gca gcc cag tgt ccc cgg cca gca agt gag gaa gac aca<br>Asp His Trp Ala Ala Gln Cys Pro Arg Pro Ala Ser Glu Glu Asp Thr<br>410                     415                    420                    425 | 1359 |
| gat gct gtt ggg cct gag cca ctg gtt cct tca cca caa cct gta cct<br>Asp Ala Val Gly Pro Glu Pro Leu Val Pro Ser Pro Gln Pro Val Pro<br>              430                       435                    440 | 1407 |
| gag gtg ccc agc ctg gac ccc acc gtg ctg cca ctc tac tcc ctg ggg<br>Glu Val Pro Ser Leu Asp Pro Thr Val Leu Pro Leu Tyr Ser Leu Gly<br>                   445                       450                    455 | 1455 |
| ccc tca ggg cag ttg gca gag acg ccg gct gag gtg ttc cag gcc ctg<br>Pro Ser Gly Gln Leu Ala Glu Thr Pro Ala Glu Val Phe Gln Ala Leu<br>              460                       465                    470 | 1503 |
| gag cag ctg ggg cac caa gcc ttt cgc cct ggg cag gag cgt gca gtc<br>Glu Gln Leu Gly His Gln Ala Phe Arg Pro Gly Gln Glu Arg Ala Val<br>475                       480                      485 | 1551 |
| atg cgg atc ctg tct ggc atc tcc acg ctg ctg gtg ctg cct aca ggt<br>Met Arg Ile Leu Ser Gly Ile Ser Thr Leu Leu Val Leu Pro Thr Gly<br>490                       495                    500                    505 | 1599 |

```
gcc ggc aag tcc ctg tgc tac cag ctc cca gcg ctg ctc tac agc cgg      1647
Ala Gly Lys Ser Leu Cys Tyr Gln Leu Pro Ala Leu Leu Tyr Ser Arg
            510                 515                 520 cgc agc ccc tgc ctc acg ttg gtc gtc tct ccc ctg ctg tca ctc atg      1695
Arg Ser Pro Cys Leu Thr Leu Val Val Ser Pro Leu Leu Ser Leu Met
                525                 530                 535 gat gac cag gtg tct ggc ctg cca ccg tgt ctc aag gcg gcc tgc ata      1743
Asp Asp Gln Val Ser Gly Leu Pro Pro Cys Leu Lys Ala Ala Cys Ile
            540                 545                 550 cac tcg ggc atg acc agg aag caa cgg gaa tct gtc ctg cag aag att      1791
His Ser Gly Met Thr Arg Lys Gln Arg Glu Ser Val Leu Gln Lys Ile
555                 560                 565 cgg gca gcc cag gta cac gtg ctg atg ctg aca cct gag gca ctg gtg      1839
Arg Ala Ala Gln Val His Val Leu Met Leu Thr Pro Glu Ala Leu Val
570                 575                 580                 585 ggg gcg gga ggc ctc cct cca gcc gca cag ctg cct cca gtt gct ttt      1887
Gly Ala Gly Gly Leu Pro Pro Ala Ala Gln Leu Pro Pro Val Ala Phe
                590                 595                 600 gcc tgc att gat gag gcc cac tgc ctc tcc cag tgg tcc cac aac ttc      1935
Ala Cys Ile Asp Glu Ala His Cys Leu Ser Gln Trp Ser His Asn Phe
            605                 610                 615 cgg ccc tgc tac ctg cgc gtc tgc aag gtg ctt cgg gag cgc atg ggc      1983
Arg Pro Cys Tyr Leu Arg Val Cys Lys Val Leu Arg Glu Arg Met Gly
                620                 625                 630 gtg cac tgc ttc ctg ggc ctc aca gcc aca gcc aca cgc cgc act gcc      2031
Val His Cys Phe Leu Gly Leu Thr Ala Thr Ala Thr Arg Arg Thr Ala
            635                 640                 645 agt gac gtg gca cag cac ctg gct gtg gct gaa gag cct gac ctc cac      2079
Ser Asp Val Ala Gln His Leu Ala Val Ala Glu Glu Pro Asp Leu His
650                 655                 660                 665 ggg cca gcc cca gtt ccc acc aac ctg cac ctt tcc gtg tcc atg gac      2127
Gly Pro Ala Pro Val Pro Thr Asn Leu His Leu Ser Val Ser Met Asp
                670                 675                 680 agg gac aca gac cag gca ctg ttg acg ctg ctg caa ggc aaa cgt ttt      2175
Arg Asp Thr Asp Gln Ala Leu Leu Thr Leu Leu Gln Gly Lys Arg Phe
            685                 690                 695 caa aac ctc gat tcc att atc att tac tgc aac cgg cgc gag gac aca      2223
Gln Asn Leu Asp Ser Ile Ile Ile Tyr Cys Asn Arg Arg Glu Asp Thr
                700                 705                 710 gag cgg atc gct gcg ctc ctc cga acc tgc ctg cac gca gcc tgg gtc      2271
Glu Arg Ile Ala Ala Leu Leu Arg Thr Cys Leu His Ala Ala Trp Val
            715                 720                 725 cca ggg tct gga ggt cgt gcc ccc aaa acc aca gcc gag gcc tac cac      2319
Pro Gly Ser Gly Gly Arg Ala Pro Lys Thr Thr Ala Glu Ala Tyr His
730                 735                 740                 745 gcg ggc atg tgc agc cgg gaa cgg cgg cgg gta cag cga gcc ttc atg      2367
Ala Gly Met Cys Ser Arg Glu Arg Arg Arg Val Gln Arg Ala Phe Met
                750                 755                 760 cag ggc cag ttg cgg gtg gtg gtg gcc acg gtg gcc ttt ggg atg ggg      2415
Gln Gly Gln Leu Arg Val Val Val Ala Thr Val Ala Phe Gly Met Gly
            765                 770                 775 ctg gac cgg cca gat gtg cgg gct gtg ctg cat ctg ggg ctg ccc cca      2463
Leu Asp Arg Pro Asp Val Arg Ala Val Leu His Leu Gly Leu Pro Pro
                780                 785                 790 agc ttc gag agc tac gtg cag gcc gtg ggc cgg gcc ggg cgt gac ggg      2511
Ser Phe Glu Ser Tyr Val Gln Ala Val Gly Arg Ala Gly Arg Asp Gly
795                 800                 805 cag cct gcc cac tgc cac ctc ttc ctg cag ccc cag ggc gaa gac ctg      2559
Gln Pro Ala His Cys His Leu Phe Leu Gln Pro Gln Gly Glu Asp Leu
```

```
                                              -continued 810                 815                 820                 825 cga gag ctg cgc aga cat gtg cac gcc gac agc acg gac ttc ctg gct         2607
Arg Glu Leu Arg Arg His Val His Ala Asp Ser Thr Asp Phe Leu Ala
                830                 835                 840 gtg aag agg ctg gta cag cgc gtg ttc cca gcc tgc acc tgc acc tgc         2655
Val Lys Arg Leu Val Gln Arg Val Phe Pro Ala Cys Thr Cys Thr Cys
                845                 850                 855 acc agg ccg ccc tcg gag cag gaa ggg gcc gtg ggt ggg gag agg cct         2703
Thr Arg Pro Pro Ser Glu Gln Glu Gly Ala Val Gly Gly Glu Arg Pro
                860                 865                 870 gtg ccc aag tac ccc cct caa gag gct gag cag ctt agc cac caa gca         2751
Val Pro Lys Tyr Pro Pro Gln Glu Ala Glu Gln Leu Ser His Gln Ala
                875                 880                 885 gcc cca gga ccc aga agg gtc tgc atg ggc cat gag cgg gca ctc cca         2799
Ala Pro Gly Pro Arg Arg Val Cys Met Gly His Glu Arg Ala Leu Pro
890                 895                 900                 905 ata cag ctt acc gta cag gct ttg gac atg ccg gag gag gcc atc gag         2847
Ile Gln Leu Thr Val Gln Ala Leu Asp Met Pro Glu Glu Ala Ile Glu
                910                 915                 920 act ttg ctg tgc tac ctg gag ctg cac cca cac cac tgg ctg gag ctg         2895
Thr Leu Leu Cys Tyr Leu Glu Leu His Pro His His Trp Leu Glu Leu
                925                 930                 935 ctg gcg acc acc tat acc cat tgc cgt ctg aac tgc cct ggg ggc cct         2943
Leu Ala Thr Thr Tyr Thr His Cys Arg Leu Asn Cys Pro Gly Gly Pro
                940                 945                 950 gcc cag ctc cag gcc ctg gcc cac agg tgt ccc cct ttg gct gtg tgc         2991
Ala Gln Leu Gln Ala Leu Ala His Arg Cys Pro Pro Leu Ala Val Cys
                955                 960                 965 ttg gcc cag cag ctg cct gag gac cca ggg caa ggc agc agc tcc gtg         3039
Leu Ala Gln Gln Leu Pro Glu Asp Pro Gly Gln Gly Ser Ser Ser Val
970                 975                 980                 985 gag ttt gac atg gtc aag ctg gtg gac tcc atg ggc tgg gag ctg gcc         3087
Glu Phe Asp Met Val Lys Leu Val Asp Ser Met Gly Trp Glu Leu Ala
                990                 995                 1000 tct gtg cgg cgg  gct ctc tgc cag ctg  cag tgg gac cac gag  ccc          3132
Ser Val Arg Arg  Ala Leu Cys Gln Leu  Gln Trp Asp His Glu  Pro
                 1005                 1010                 1015 agg aca ggt gtg  cgg cgt ggg aca ggg  gtg ctt gtg gag ttc  agt          3177
Arg Thr Gly Val  Arg Arg Gly Thr Gly  Val Leu Val Glu Phe  Ser
                 1020                 1025                 1030 gag ctg gcc ttc  cac ctt cgc agc ccg  ggg gac ctg acc gct  gag          3222
Glu Leu Ala Phe  His Leu Arg Ser Pro  Gly Asp Leu Thr Ala  Glu
                 1035                 1040                 1045 gag aag gac cag  ata tgt gac ttc ctc  tat ggc cgt gtg cag  gcc          3267
Glu Lys Asp Gln  Ile Cys Asp Phe Leu  Tyr Gly Arg Val Gln  Ala
                 1050                 1055                 1060 cgg gag cgc cag  gcc ctg gcc cgt ctg  cgc aga acc ttc cag  gcc          3312
Arg Glu Arg Gln  Ala Leu Ala Arg Leu  Arg Arg Thr Phe Gln  Ala
                 1065                 1070                 1075 ttt cac agc gta  gcc ttc ccc agc tgc  ggg ccc tgc ctg gag  cag          3357
Phe His Ser Val  Ala Phe Pro Ser Cys  Gly Pro Cys Leu Glu  Gln
                 1080                 1085                 1090 cag gat gag gag  cgc agc acc agg ctc  aag gac ctg ctc ggc  cgc          3402
Gln Asp Glu Glu  Arg Ser Thr Arg Leu  Lys Asp Leu Leu Gly  Arg
                 1095                 1100                 1105 tac ttt gag gaa  gag gaa ggg cag gag  ccg gga ggc atg gag  gac          3447
Tyr Phe Glu Glu  Glu Glu Gly Gln Glu  Pro Gly Gly Met Glu  Asp
                 1110                 1115                 1120 gca cag ggc ccc  gag cca ggg cag gcc  aga ctc cag gat tgg  gag          3492
```

```
                                                         -continued

Ala Gln Gly Pro  Glu Pro Gly Gln  Ala Arg Leu Gln  Asp Trp Glu
              1125              1130              1135 gac cag gtc cgc  tgc gac atc cgc  cag ttc ctg tcc  ctg agg cca      3537
Asp Gln Val Arg  Cys Asp Ile Arg  Gln Phe Leu Ser  Leu Arg Pro
              1140              1145              1150 gag gag aag ttc  tcc agc agg gct  gtg gcc cgc atc  ttc cac ggc      3582
Glu Glu Lys Phe  Ser Ser Arg Ala  Val Ala Arg Ile  Phe His Gly
              1155              1160              1165 atc gga agc ccc  tgc tac ccg gcc  cag gtg tac ggg  cag gac cga      3627
Ile Gly Ser Pro  Cys Tyr Pro Ala  Gln Val Tyr Gly  Gln Asp Arg
              1170              1175              1180 cgc ttc tgg aga  aaa tac ctg cac  ctg agc ttc cat  gcc ctg gtg      3672
Arg Phe Trp Arg  Lys Tyr Leu His  Leu Ser Phe His  Ala Leu Val
              1185              1190              1195 ggc ctg gcc acg  gaa gag ctc ctg  cag gtg gcc cgc tgactgcact        3718
Gly Leu Ala Thr  Glu Glu Leu Leu  Gln Val Ala Arg
              1200              1205 gcattggggg atgtcgggta gagctggggt tgtcagaggc tagggcagtg actgaggacc   3778
tgggcaaaac ctgccacagg gtgtgggaac gaggaggctc caaaatgcag aataaaaaat   3838
gctcactttg tt                                                      3850

<210> SEQ ID NO 2
<211> LENGTH: 1208
<212> TYPE: PRT
<213> ORGANISM: Homo sapiens

<400> SEQUENCE: 2

Met Glu Arg Leu  Arg Asp Val Arg  Glu Arg Leu Gln  Ala Trp Glu Arg
1                5                10               15

Ala Phe Arg Arg  Gln Arg Gly Arg  Arg Pro Ser Gln  Asp Asp Val Glu
              20               25               30

Ala Ala Pro Glu  Glu Thr Arg Ala  Leu Tyr Arg Glu  Tyr Arg Thr Leu
              35               40               45

Lys Arg Thr Thr  Gly Gln Ala Gly  Gly Leu Arg Ser  Ser Glu Ser
              50               55               60

Leu Pro Ala Ala  Ala Glu Glu Ala  Pro Glu Pro Arg  Cys Trp Gly Pro
65                70               75               80

His Leu Asn Arg  Ala Ala Thr Lys  Ser Pro Gln Pro  Thr Pro Gly Arg
              85               90               95

Ser Arg Gln Gly  Ser Val Pro Tyr  Gly Gln Arg Leu  Lys Ala Asn
              100              105              110

Leu Lys Gly Thr  Leu Gln Ala Gly  Pro Ala Leu Gly  Arg Arg Pro Trp
              115              120              125

Pro Leu Gly Arg  Ala Ser Ser Lys  Ala Ser Thr Pro  Lys Pro Pro Gly
              130              135              140

Thr Gly Pro Val  Pro Ser Phe Ala  Glu Lys Val Ser  Asp Glu Pro Pro
145              150              155              160

Gln Leu Pro Glu  Pro Gln Pro Arg  Pro Gly Arg Leu  Gln His Leu Gln
              165              170              175

Ala Ser Leu Ser  Gln Arg Leu Gly  Ser Leu Asp Pro  Gly Trp Leu Gln
              180              185              190

Arg Cys His Ser  Glu Val Pro Asp  Phe Leu Gly Ala  Pro Lys Ala Cys
              195              200              205

Arg Pro Asp Leu  Gly Ser Glu Ser  Gln Leu Leu Ile  Pro Gly Glu
              210              215              220
```

```
Ser Ala Val Leu Gly Pro Gly Ala Gly Ser Gln Gly Pro Glu Ala Ser
225                 230                 235                 240

Ala Phe Gln Glu Val Ser Ile Arg Val Gly Ser Pro Gln Pro Ser Ser
            245                 250                 255

Ser Gly Gly Glu Lys Arg Arg Trp Asn Glu Glu Pro Trp Glu Ser Pro
            260                 265                 270

Ala Gln Val Gln Gln Glu Ser Ser Gln Ala Gly Pro Pro Ser Glu Gly
            275                 280                 285

Ala Gly Ala Val Ala Val Glu Glu Asp Pro Pro Gly Glu Pro Val Gln
            290                 295                 300

Ala Gln Pro Pro Gln Pro Cys Ser Ser Pro Ser Asn Pro Arg Tyr His
305                 310                 315                 320

Gly Leu Ser Pro Ser Ser Gln Ala Arg Ala Gly Lys Ala Glu Gly Thr
                325                 330                 335

Ala Pro Leu His Ile Phe Pro Arg Leu Ala Arg His Asp Arg Gly Asn
                340                 345                 350

Tyr Val Arg Leu Asn Met Lys Gln Lys His Tyr Val Arg Gly Arg Ala
                355                 360                 365

Leu Arg Ser Arg Leu Leu Arg Lys Gln Ala Trp Lys Gln Lys Trp Arg
370                 375                 380

Lys Lys Gly Glu Cys Phe Gly Gly Gly Ala Thr Val Thr Thr Lys
385                 390                 395                 400

Glu Ser Cys Phe Leu Asn Glu Gln Phe Asp His Trp Ala Ala Gln Cys
                405                 410                 415

Pro Arg Pro Ala Ser Glu Glu Asp Thr Asp Ala Val Gly Pro Glu Pro
                420                 425                 430

Leu Val Pro Ser Pro Gln Pro Val Pro Glu Val Pro Ser Leu Asp Pro
                435                 440                 445

Thr Val Leu Pro Leu Tyr Ser Leu Gly Pro Ser Gly Gln Leu Ala Glu
    450                 455                 460

Thr Pro Ala Glu Val Phe Gln Ala Leu Glu Gln Leu Gly His Gln Ala
465                 470                 475                 480

Phe Arg Pro Gly Gln Glu Arg Ala Val Met Arg Ile Leu Ser Gly Ile
                485                 490                 495

Ser Thr Leu Leu Val Leu Pro Thr Gly Ala Gly Lys Ser Leu Cys Tyr
                500                 505                 510

Gln Leu Pro Ala Leu Leu Tyr Ser Arg Arg Ser Pro Cys Leu Thr Leu
                515                 520                 525

Val Val Ser Pro Leu Leu Ser Leu Met Asp Asp Gln Val Ser Gly Leu
530                 535                 540

Pro Pro Cys Leu Lys Ala Ala Cys Ile His Ser Gly Met Thr Arg Lys
545                 550                 555                 560

Gln Arg Glu Ser Val Leu Gln Lys Ile Arg Ala Ala Gln Val His Val
                565                 570                 575

Leu Met Leu Thr Pro Glu Ala Leu Val Gly Ala Gly Leu Pro Pro
                580                 585                 590

Ala Ala Gln Leu Pro Pro Val Ala Phe Ala Cys Ile Asp Glu Ala His
            595                 600                 605

Cys Leu Ser Gln Trp Ser His Asn Phe Arg Pro Cys Tyr Leu Arg Val
            610                 615                 620

Cys Lys Val Leu Arg Glu Arg Met Gly Val His Cys Phe Leu Gly Leu
625                 630                 635                 640

Thr Ala Thr Ala Thr Arg Arg Thr Ala Ser Asp Val Ala Gln His Leu
```

```
                  645            650            655
Ala Val Ala Glu Glu Pro Asp Leu His Gly Pro Ala Pro Val Pro Thr
            660            665            670
Asn Leu His Leu Ser Val Ser Met Asp Arg Asp Thr Asp Gln Ala Leu
            675            680            685
Leu Thr Leu Leu Gln Gly Lys Arg Phe Gln Asn Leu Asp Ser Ile Ile
            690            695            700
Ile Tyr Cys Asn Arg Arg Glu Asp Thr Glu Arg Ile Ala Ala Leu Leu
705            710            715            720
Arg Thr Cys Leu His Ala Ala Trp Val Pro Gly Ser Gly Gly Arg Ala
            725            730            735
Pro Lys Thr Thr Ala Glu Ala Tyr His Ala Gly Met Cys Ser Arg Glu
            740            745            750
Arg Arg Arg Val Gln Arg Ala Phe Met Gln Gly Gln Leu Arg Val Val
            755            760            765
Val Ala Thr Val Ala Phe Gly Met Gly Leu Asp Arg Pro Asp Val Arg
            770            775            780
Ala Val Leu His Leu Gly Leu Pro Pro Ser Phe Glu Ser Tyr Val Gln
785            790            795            800
Ala Val Gly Arg Ala Gly Arg Asp Gly Gln Pro Ala His Cys His Leu
            805            810            815
Phe Leu Gln Pro Gln Gly Glu Asp Leu Arg Glu Leu Arg Arg His Val
            820            825            830
His Ala Asp Ser Thr Asp Phe Leu Ala Val Lys Arg Leu Val Gln Arg
            835            840            845
Val Phe Pro Ala Cys Thr Cys Thr Cys Thr Arg Pro Pro Ser Glu Gln
            850            855            860
Glu Gly Ala Val Gly Gly Glu Arg Pro Val Pro Lys Tyr Pro Pro Gln
865            870            875            880
Glu Ala Glu Gln Leu Ser His Gln Ala Ala Pro Gly Pro Arg Arg Val
            885            890            895
Cys Met Gly His Glu Arg Ala Leu Pro Ile Gln Leu Thr Val Gln Ala
            900            905            910
Leu Asp Met Pro Glu Glu Ala Ile Glu Thr Leu Leu Cys Tyr Leu Glu
            915            920            925
Leu His Pro His His Trp Leu Glu Leu Leu Ala Thr Thr Tyr Thr His
            930            935            940
Cys Arg Leu Asn Cys Pro Gly Gly Pro Ala Gln Leu Gln Ala Leu Ala
945            950            955            960
His Arg Cys Pro Pro Leu Ala Val Cys Leu Ala Gln Gln Leu Pro Glu
            965            970            975
Asp Pro Gly Gln Gly Ser Ser Ser Val Glu Phe Asp Met Val Lys Leu
            980            985            990
Val Asp Ser Met Gly Trp Glu Leu  Ala Ser Val Arg Arg  Ala Leu Cys
        995            1000           1005
Gln Leu Gln Trp Asp His Glu  Pro Arg Thr Gly Val  Arg Arg Gly
    1010           1015           1020
Thr Gly  Val Leu Val Glu Phe  Ser Glu Leu Ala Phe  His Leu Arg
    1025           1030           1035
Ser Pro  Gly Asp Leu Thr Ala  Glu Glu Lys Asp Gln  Ile Cys Asp
    1040           1045           1050
Phe Leu  Tyr Gly Arg Val Gln  Ala Arg Glu Arg Gln  Ala Leu Ala
    1055           1060           1065
```

-continued

```
Arg Leu Arg Arg Thr Phe Gln Ala Phe His Ser Val Ala Phe Pro
    1070                1075                1080

Ser Cys Gly Pro Cys Leu Glu Gln Gln Asp Glu Glu Arg Ser Thr
    1085                1090                1095

Arg Leu Lys Asp Leu Leu Gly Arg Tyr Phe Glu Glu Glu Gly
    1100                1105                1110

Gln Glu Pro Gly Gly Met Glu Asp Ala Gln Gly Pro Glu Pro Gly
    1115                1120                1125

Gln Ala Arg Leu Gln Asp Trp Glu Asp Gln Val Arg Cys Asp Ile
    1130                1135                1140

Arg Gln Phe Leu Ser Leu Arg Pro Glu Glu Lys Phe Ser Ser Arg
    1145                1150                1155

Ala Val Ala Arg Ile Phe His Gly Ile Gly Ser Pro Cys Tyr Pro
    1160                1165                1170

Ala Gln Val Tyr Gly Gln Asp Arg Arg Phe Trp Arg Lys Tyr Leu
    1175                1180                1185

His Leu Ser Phe His Ala Leu Val Gly Leu Ala Thr Glu Glu Leu
    1190                1195                1200

Leu Gln Val Ala Arg
    1205

<210> SEQ ID NO 3
<211> LENGTH: 24
<212> TYPE: DNA
<213> ORGANISM: Artificial Sequence
<220> FEATURE:
<223> OTHER INFORMATION: SENSE PRIMER

<400> SEQUENCE: 3
caccaacctg cacctttccg tgtc                                           24

<210> SEQ ID NO 4
<211> LENGTH: 24
<212> TYPE: DNA
<213> ORGANISM: Artificial Sequence
<220> FEATURE:
<223> OTHER INFORMATION: ANTISENSE PRIMER

<400> SEQUENCE: 4
agccccatcc caaaagccac cgtg                                           24

<210> SEQ ID NO 5
<211> LENGTH: 24
<212> TYPE: DNA
<213> ORGANISM: Artificial Sequence
<220> FEATURE:
<223> OTHER INFORMATION: PRIMERS FOR SEQUENCING

<400> SEQUENCE: 5
cgccagggtt ttcccagtca cgac                                           24

<210> SEQ ID NO 6
<211> LENGTH: 22
<212> TYPE: DNA
<213> ORGANISM: Artificial Sequence
<220> FEATURE:
<223> OTHER INFORMATION: PRIMERS FOR SEQUENCING

<400> SEQUENCE: 6
tcacacagga aacagctatg ac                                             22
```

```
<210> SEQ ID NO 7
<211> LENGTH: 24
<212> TYPE: DNA
<213> ORGANISM: Artificial Sequence
<220> FEATURE:
<223> OTHER INFORMATION: PRIMERS FOR SEQUENCING

<400> SEQUENCE: 7
aatctgggac ctcactgtga catc                                              24

<210> SEQ ID NO 8
<211> LENGTH: 24
<212> TYPE: DNA
<213> ORGANISM: Artificial Sequence
<220> FEATURE:
<223> OTHER INFORMATION: PRIMERS FOR SEQUENCING

<400> SEQUENCE: 8
tcatctaagg catccacccc aaag                                              24

<210> SEQ ID NO 9
<211> LENGTH: 24
<212> TYPE: DNA
<213> ORGANISM: Artificial Sequence
<220> FEATURE:
<223> OTHER INFORMATION: PRIMERS FOR SEQUENCING

<400> SEQUENCE: 9
tcacaacttc tgatccctgg tgag                                              24

<210> SEQ ID NO 10
<211> LENGTH: 24
<212> TYPE: DNA
<213> ORGANISM: Artificial Sequence
<220> FEATURE:
<223> OTHER INFORMATION: PRIMERS FOR SEQUENCING

<400> SEQUENCE: 10
ctcagcccct ccagtcaagc tagg                                              24

<210> SEQ ID NO 11
<211> LENGTH: 24
<212> TYPE: DNA
<213> ORGANISM: Artificial Sequence
<220> FEATURE:
<223> OTHER INFORMATION: PRIMERS FOR SEQUENCING

<400> SEQUENCE: 11
gtttcctgaa cgagcagttc gatc                                              24

<210> SEQ ID NO 12
<211> LENGTH: 24
<212> TYPE: DNA
<213> ORGANISM: Artificial Sequence
<220> FEATURE:
<223> OTHER INFORMATION: PRIMERS FOR SEQUENCING

<400> SEQUENCE: 12
ctgggcagga gcgtgcagtc atgc                                              24

<210> SEQ ID NO 13
<211> LENGTH: 24
<212> TYPE: DNA
<213> ORGANISM: Artificial Sequence
<220> FEATURE:
<223> OTHER INFORMATION: PRIMERS FOR SEQUENCING
```

<400> SEQUENCE: 13
gctgcctcca gttgcttttg cctg     24

<210> SEQ ID NO 14
<211> LENGTH: 24
<212> TYPE: DNA
<213> ORGANISM: Artificial Sequence
<220> FEATURE:
<223> OTHER INFORMATION: PRIMERS FOR SEQUENCING

<400> SEQUENCE: 14
ggacacagac caggcactgt tgac     24

<210> SEQ ID NO 15
<211> LENGTH: 24
<212> TYPE: DNA
<213> ORGANISM: Artificial Sequence
<220> FEATURE:
<223> OTHER INFORMATION: PRIMERS FOR SEQUENCING

<400> SEQUENCE: 15
gggtacagcg agccttcatg cagg     24

<210> SEQ ID NO 16
<211> LENGTH: 24
<212> TYPE: DNA
<213> ORGANISM: Artificial Sequence
<220> FEATURE:
<223> OTHER INFORMATION: PRIMERS FOR SEQUENCING

<400> SEQUENCE: 16
tcctggctgt gaagaggctg gtac     24

<210> SEQ ID NO 17
<211> LENGTH: 22
<212> TYPE: DNA
<213> ORGANISM: Artificial Sequence
<220> FEATURE:
<223> OTHER INFORMATION: PRIMERS FOR SEQUENCING

<400> SEQUENCE: 17
cagcttaccg tacaggcttt gg     22

<210> SEQ ID NO 18
<211> LENGTH: 22
<212> TYPE: DNA
<213> ORGANISM: Artificial Sequence
<220> FEATURE:
<223> OTHER INFORMATION: PRIMERS FOR SEQUENCING

<400> SEQUENCE: 18
ggggtgcttg tggagttcag tg     22

<210> SEQ ID NO 19
<211> LENGTH: 22
<212> TYPE: DNA
<213> ORGANISM: Artificial Sequence
<220> FEATURE:
<223> OTHER INFORMATION: PRIMERS FOR SEQUENCING

<400> SEQUENCE: 19
caggccagac tccaggattg gg     22

<210> SEQ ID NO 20

```
<211> LENGTH: 27
<212> TYPE: DNA
<213> ORGANISM: Artificial Sequence
<220> FEATURE:
<223> OTHER INFORMATION: PRIMER AP1

<400> SEQUENCE: 20
ccatcctaat acgactcact atagggc                                          27

<210> SEQ ID NO 21
<211> LENGTH: 23
<212> TYPE: DNA
<213> ORGANISM: Artificial Sequence
<220> FEATURE:
<223> OTHER INFORMATION: AP2

<400> SEQUENCE: 21
actcactata gggctcgagc ggc                                              23

<210> SEQ ID NO 22
<211> LENGTH: 24
<212> TYPE: DNA
<213> ORGANISM: Artificial Sequence
<220> FEATURE:
<223> OTHER INFORMATION: PRIMER 5' GSP1

<400> SEQUENCE: 22
gccttgcagc agcgtcaaca gtgc                                             24

<210> SEQ ID NO 23
<211> LENGTH: 24
<212> TYPE: DNA
<213> ORGANISM: Artificial Sequence
<220> FEATURE:
<223> OTHER INFORMATION: PRIMER 5' GSP2

<400> SEQUENCE: 23
tggacacgga aggtgcagg ttgg                                              24

<210> SEQ ID NO 24
<211> LENGTH: 24
<212> TYPE: DNA
<213> ORGANISM: Artificial Sequence
<220> FEATURE:
<223> OTHER INFORMATION: PRIMER 3'GSP1

<400> SEQUENCE: 24
gttgacgctg ctgcaaggca aacg                                             24

<210> SEQ ID NO 25
<211> LENGTH: 24
<212> TYPE: DNA
<213> ORGANISM: Artificial Sequence
<220> FEATURE:
<223> OTHER INFORMATION: PRIMER 3' GSP2

<400> SEQUENCE: 25
catctcatgg aatgatcctg tcgg                                             24

<210> SEQ ID NO 26
<211> LENGTH: 30
<212> TYPE: RNA
<213> ORGANISM: Artificial Sequence
<220> FEATURE:
<223> OTHER INFORMATION: OLIGO RNA ADAPTER

<400> SEQUENCE: 26
```
cgaaucguaa ccguucguac gagaaucgcu                                    30

<210> SEQ ID NO 27
<211> LENGTH: 23
<212> TYPE: DNA
<213> ORGANISM: Artificial Sequence
<220> FEATURE:
<223> OTHER INFORMATION: SENSE PRIMER FIRST ROUND

<400> SEQUENCE: 27
cgaatcgtaa ccgttcgtac gag                                           23

<210> SEQ ID NO 28
<211> LENGTH: 26
<212> TYPE: DNA
<213> ORGANISM: Artificial Sequence
<220> FEATURE:
<223> OTHER INFORMATION: SENSE PRIMER NESTED

<400> SEQUENCE: 28
atcgtaaccg ttcgtacgag aatcgc                                        26

<210> SEQ ID NO 29
<211> LENGTH: 24
<212> TYPE: DNA
<213> ORGANISM: Artificial Sequence
<220> FEATURE:
<223> OTHER INFORMATION: ANTISENSE PRIMER FIRST ROUND

<400> SEQUENCE: 29
taggctgtgg actcttggtc gcag                                          24

<210> SEQ ID NO 30
<211> LENGTH: 24
<212> TYPE: DNA
<213> ORGANISM: Artificial Sequence
<220> FEATURE:
<223> OTHER INFORMATION: ANTISENSE PRIMER NESTED

<400> SEQUENCE: 30
ttggtcgcag cccgattcag atgg                                          24

<210> SEQ ID NO 31
<211> LENGTH: 321
<212> TYPE: DNA
<213> ORGANISM: Artificial Sequence
<220> FEATURE:
<223> OTHER INFORMATION: RECQ4 PARTIAL cDNA

<400> SEQUENCE: 31
caccaacctg cacctttccg tgtccatgga cagggacaca gaccaggcac tgttgacgct      60
gctgcaaggc aaacgttttc aaaacctcga ttccattatc atttactgca accgcgcga     120 ggacacagag cggatcgctg cgctcctccg aacctgcctg cacgcagcct gggtcccagg     180
gtctggaggt cgtgccccca aaaccacagc cgaggcctac cacgcgggca tgtgcagccg     240
ggaacggcgg cgggtacagc gagccttcat gcagggccag ttgcgggtgg tggtggccac     300
ggtggccttt gggatggggc t                                             321

<210> SEQ ID NO 32
<211> LENGTH: 1954
<212> TYPE: DNA
<213> ORGANISM: Artificial Sequence
<220> FEATURE:

<223> OTHER INFORMATION: RECQ4 5' RACE PRODUCT

<400> SEQUENCE: 32

```
gacgacgtgg aggcggcgcc ggaggagacc cgcgcgctct accgggagta ccgcactctg    60
aagcgtacca cgggccaggc cggcggcggg ctccgcagct ccgagtcgct ccccgcggcg   120
gccgaagagg cgccagagcc ccgctgctgg gggccccatc tgaatcgggc tgcgaccaag   180
agtccacagc ctacgccagg gcggagccgc cagggctcgg tgccggacta cgggcagcgg   240
ctcaaggcca atctgaaagg caccctgcag gccggaccag ccctgggccg cagaccgtgg   300
cctctaggaa gagcctcatc taaggcatcc accccaaagc ccccaggtac agggcctgtc   360
ccctcctttg cagaaaaagt cagtgatgag cctccacagc tccctgagcc ccagccaagg   420
ccaggccggc tccagcatct gcaggcatcc ctgagccagc ggctgggctc cctagatcct   480
ggctggttac agcgatgtca cagtgaggtc ccagattttc tggggcccc caaagcctgc    540
aggcctgatc taggctcaga ggaatcacaa cttctgatcc ctggtgagtc ggctgtcctt   600
ggtcctggtg ctggctccca gggcccagag gcttcagcct ccaagaagt cagcatccgt    660
gtggggagcc cccagcccag cagcagtgga ggcgagaagc ggagatggaa cgaggagccc   720
tgggagagcc ccgcacaggt ccagcaggag agcagccaag ctggaccccc atcggagggg   780
gctggggctg tagcagttga ggaagaccct ccaggggaac ctgtacaggc acagccacct   840
cagccctgca gcagcccatc gaaccccagg taccacggac tcagcccctc cagtcaagct   900
agggctggga aggctgaggg cacagccccc ctgcacatct tccctcggct ggcccgccat   960
gacaggggca attacgtacg gctcaacatg aagcagaaac actacgtgcg gggccgggca  1020
ctccgtagca ggctcctccg caagcaggca tggaagcaga agtggcggaa gaaggggag   1080
tgttttgggg gtggtggtgc cacagtcaca accaaggagt cttgtttcct gaacgagcag  1140
ttcgatcact gggcagccca gtgtccccgg ccagcaagtg aggaagacac agatgctgtt  1200
gggcctgagc cactggttcc ttcaccacaa cctgtacctg aggtgcccag cctggacccc  1260
accgtgctgc cactctactc cctggggccc tcagggcagt tggcagagac gccggctgag  1320
gtgttccagg ccctggagca gctggggcac caagcctttc gccctgggca ggagcgtgca  1380
gtcatgcgga tcctgtctgg catctccacg ctgctggtgc tgcctacagg tgccggcaag  1440
tccctgtgct accagctccc agcgctgctc tacagccggc gcagcccctg cctcacgttg  1500
gtcgtctctc ccctgctgtc actcatggat gaccaggtgt ctggcctgcc accgtgtctc  1560
aaggcggcct gcatacactc gggcatgacc aggaagcaac gggaatctgt cctgcagaag  1620
attcgggcag cccaggtaca cgtgctgatg ctgacacctg aggcactggt gggggcggga  1680
ggcctccctc cagccgcaca gctgcctcca gttgcttttg cctgcattga tgaggcccac  1740
tgcctctccc agtggtccca caacttccgg ccctgctacc tgcgcgtctg caaggtgctt  1800
cgggagcgca tgggcgtgca ctgcttcctg ggcctcacag ccacagccac acgccgcact  1860
gccagtgacg tggcacagca cctggctgtg gctgaagagc ctgacctcca cgggccagcc  1920
ccagttccca ccaacctgca cctttccgtg tcca                              1954
```

<210> SEQ ID NO 33
<211> LENGTH: 1503
<212> TYPE: DNA
<213> ORGANISM: Artificial Sequence
<220> FEATURE:
<223> OTHER INFORMATION: RECQ4 3' RACE PRODUCT

<400> SEQUENCE: 33

```
gggtacagcg agccttcatg cagggccagt tgcgggtggt ggtggccacg gtggcctttg    60
ggatggggct ggaccggcca gatgtgcggg ctgtgctgca tctggggctg cccccaagct   120
tcgagagcta cgtgcaggcc gtgggccggg ccggcgtga cgggcagcct gcccactgcc   180
acctcttcct gcagccccag ggcgaagacc tgcgagagct cgcagacat gtgcacgccg   240 acagcacgga cttcctggct gtgaagaggc tggtacagcg cgtgttccca gcctgcacct   300
gcacctgcac caggccgccc tcggagcagg aaggggccgt gggtggggag aggcctgtgc   360
ccaagtaccc ccctcaagag gctgagcagc ttagccacca agcagcccca ggacccagaa   420
gggtctgcat gggccatgag cgggcactcc aatacagct taccgtacag gctttggaca   480
tgccggagga ggccatcgag actttgctgt gctacctgga gctgcaccca ccactggc    540 tggagctgct ggcgaccacc tatacccatt gccgtctgaa ctgccctggg ggccctgccc   600
agctccaggc cctggcccac aggtgtcccc ctttggctgt gtgcttggcc cagcagctgc   660
ctgaggaccc agggcaaggc agcagctccg tggagtttga catggtcaag ctggtggact   720
ccatgggctg ggagctggcc tctgtgcggg ggctctctg ccagctgcag tgggaccacg    780
agcccaggac aggtgtgcgg cgtgggacag gggtgcttgt ggagttcagt gagctggcct   840
tccaccttcg cagcccgggg gacctgaccg ctgaggagaa ggaccagata tgtgacttcc   900
tctatggccg tgtgcaggcc cgggagcgcc aggccctggc ccgtctgcgc agaaccttcc   960
aggcctttca cagcgtagcc ttccccagct gcgggccctg cctggagcag caggatgagg  1020
agcgcagcac caggctcaag gacctgctcg gccgctactt tgaggaagag gaagggcagg  1080
agccgggagg catggaggac gcacagggcc ccgagccagg gcaggccaga ctccaggatt  1140
gggaggacca ggtccgctgc gacatccgcc agttcctgtc cctgaggcca gaggagaagt  1200
tctccagcag ggctgtggcc cgcatcttcc acggcatcgg aagccctgc tacccggccc   1260 aggtgtacgg gcaggaccga cgcttctgga gaaaatacct gcacctgagc ttccatgccc  1320
tggtgggcct ggccacggaa gagctcctgc aggtggcccg ctgactgcac tgcattgggg  1380
gatgtcgggt agagctgggg ttgtcagagg ctagggcagt gactgaggac ctgggcaaaa  1440
cctgccacag ggtgtgggaa cgaggaggct ccaaaatgca gaataaaaaa tgctcacttt  1500
gtt                                                              1503
```

<210> SEQ ID NO 34
<211> LENGTH: 347
<212> TYPE: DNA
<213> ORGANISM: Artificial Sequence
<220> FEATURE:
<223> OTHER INFORMATION: RECQ4 TRANSCRIPTION ORIGIN REGION

<400> SEQUENCE: 34

```
gcattggctg tcggccccg cgacggctgc gcgggagatt cgctggacga tcgcaagcgc    60
ggaggccggg cggcgcgcg cgccatggag cggctgcggg acgtgcggga gcggctgcag   120
gcgtgggagc gcgcgttccg acggcagcgc gggcggcgac cgagccagga cgacgtggag   180
gcggcgccgg aggagacccg cgcgctctac cgggagtacc gcactctgaa cgtaccacg    240 ggccaggccg gcgcgggct ccgcagctcc gagtcgctcc ccgcggcggc cgaagaggcg    300
ccagagcccc gctgctgggg gccccatctg aatcgggctg cgaccaa                347
```

<210> SEQ ID NO 35
<211> LENGTH: 24
<212> TYPE: DNA

```
<213> ORGANISM: Artificial Sequence
<220> FEATURE:
<223> OTHER INFORMATION: PRIMERS FOR THE RECQ4 GENE

<400> SEQUENCE: 35
gacggctgcg cgggagattc gctg                                          24

<210> SEQ ID NO 36
<211> LENGTH: 24
<212> TYPE: DNA
<213> ORGANISM: Artificial Sequence
<220> FEATURE:
<223> OTHER INFORMATION: PRIMERS FOR THE RECQ4 GENE

<400> SEQUENCE: 36
caggttttgc ccaggtcctc agtc                                          24

<210> SEQ ID NO 37
<211> LENGTH: 361
<212> TYPE: PRT
<213> ORGANISM: Homo sapiens

<400> SEQUENCE: 37
```

Gln Ala Leu Glu Gln Leu Gly His Gln Ala Phe Arg Pro Gly Gln Glu
1               5                   10                  15

Arg Ala Val Met Arg Ile Leu Ser Gly Ile Ser Thr Leu Leu Val Leu
            20                  25                  30

Pro Thr Gly Ala Gly Lys Ser Leu Cys Tyr Gln Leu Pro Ala Leu Leu
        35                  40                  45

Tyr Ser Arg Arg Ser Pro Cys Leu Thr Leu Val Val Ser Pro Leu Leu
50                  55                  60

Ser Leu Met Asp Asp Gln Val Ser Gly Leu Pro Pro Cys Leu Lys Ala
65                  70                  75                  80

Ala Cys Ile His Ser Gly Met Thr Arg Lys Gln Arg Glu Ser Val Leu
                85                  90                  95

Gln Lys Ile Arg Ala Ala Gln Val His Val Leu Met Leu Thr Pro Glu
            100                 105                 110

Ala Leu Val Gly Ala Gly Gly Leu Pro Pro Ala Ala Gln Leu Pro Pro
        115                 120                 125

Val Ala Phe Ala Cys Ile Asp Glu Ala His Cys Leu Ser Gln Trp Ser
130                 135                 140

His Asn Phe Arg Pro Cys Tyr Leu Arg Val Cys Lys Val Leu Arg Glu
145                 150                 155                 160

Arg Met Gly Val His Cys Phe Leu Gly Leu Thr Ala Thr Ala Thr Arg
                165                 170                 175

Arg Thr Ala Ser Asp Val Ala Gln His Leu Ala Val Ala Glu Glu Pro
            180                 185                 190

Asp Leu His Gly Pro Ala Pro Val Pro Thr Asn Leu His Leu Ser Val
        195                 200                 205

Ser Met Asp Arg Asp Thr Asp Gln Ala Leu Leu Thr Leu Leu Gln Gly
    210                 215                 220

Lys Arg Phe Gln Asn Leu Asp Ser Ile Ile Tyr Cys Asn Arg Arg
225                 230                 235                 240

Glu Asp Thr Glu Arg Ile Ala Ala Leu Leu Arg Thr Cys Leu His Ala
                245                 250                 255

Ala Trp Val Pro Gly Ser Gly Arg Ala Pro Lys Thr Thr Ala Glu
            260                 265                 270

```
Ala Tyr His Ala Gly Met Cys Ser Arg Glu Arg Arg Val Gln Arg
        275                 280                 285

Ala Phe Met Gln Gly Gln Leu Arg Val Val Ala Thr Val Ala Phe
        290                 295                 300

Gly Met Gly Leu Asp Arg Pro Asp Val Arg Ala Val Leu His Leu Gly
305                 310                 315                 320

Leu Pro Pro Ser Phe Glu Ser Tyr Val Gln Ala Val Gly Arg Ala Gly
                325                 330                 335

Arg Asp Gly Gln Pro Ala His Cys His Leu Phe Leu Gln Pro Gln Gly
            340                 345                 350

Glu Asp Leu Arg Glu Leu Arg Arg His
        355                 360

<210> SEQ ID NO 38
<211> LENGTH: 334
<212> TYPE: PRT
<213> ORGANISM: Escherichia coli

<400> SEQUENCE: 38

Phe Gly Tyr Gln Gln Phe Arg Pro Gly Gln Glu Glu Ile Ile Asp Thr
1               5                   10                  15

Val Leu Ser Gly Arg Asp Cys Leu Val Val Met Pro Thr Gly Gly Gly
            20                  25                  30

Lys Ser Leu Cys Tyr Gln Ile Pro Ala Leu Leu Leu Asn Gly Leu Thr
        35                  40                  45

Val Val Val Ser Pro Leu Ile Ser Leu Met Lys Asp Gln Val Asp Gln
    50                  55                  60

Leu Gln Ala Asn Gly Val Ala Ala Ala Cys Leu Asn Ser Thr Gln Thr
65                  70                  75                  80

Arg Glu Gln Gln Leu Glu Val Met Thr Gly Cys Arg Thr Gly Gln Ile
                85                  90                  95

Arg Leu Leu Tyr Ile Ala Pro Glu Arg Leu Met Leu Asp Asn Phe Leu
            100                 105                 110

Glu His Leu Ala His Trp Asn Pro Val Leu Leu Ala Val Asp Glu Ala
        115                 120                 125

His Cys Ile Ser Gln Trp Gly His Asp Phe Arg Pro Glu Tyr Ala Ala
    130                 135                 140

Leu Gly Gln Leu Arg Gln Arg Phe Pro Thr Leu Pro Phe Met Ala Leu
145                 150                 155                 160

Thr Ala Thr Ala Asp Asp Thr Thr Arg Gln Asp Ile Val Arg Leu Leu
                165                 170                 175

Gly Leu Asn Asp Pro Leu Ile Gln Ile Ser Ser Phe Asp Arg Pro Asn
            180                 185                 190

Ile Arg Tyr Met Leu Met Glu Lys Phe Lys Pro Leu Asp Gln Leu Met
        195                 200                 205

Arg Tyr Val Gln Glu Gln Arg Gly Lys Ser Gly Ile Ile Tyr Cys Asn
    210                 215                 220

Ser Arg Ala Lys Val Glu Asp Thr Ala Ala Arg Leu Gln Ser Lys Gly
225                 230                 235                 240

Ile Ser Ala Ala Ala Tyr His Ala Gly Leu Glu Asn Asn Val Arg Ala
                245                 250                 255

Asp Val Gln Glu Lys Phe Gln Arg Asp Asp Leu Gln Ile Val Val Ala
            260                 265                 270

Thr Val Ala Phe Gly Met Gly Ile Asn Lys Pro Asn Val Arg Phe Val
        275                 280                 285
```

```
Val His Phe Asp Ile Pro Arg Asn Ile Glu Ser Tyr Tyr Gln Glu Thr
    290                 295                 300
Gly Arg Ala Gly Arg Asp Gly Leu Pro Ala Glu Ala Met Leu Phe Tyr
305                 310                 315                 320
Asp Pro Ala Asp Met Ala Trp Leu Arg Arg Cys Leu Glu Glu
                325                 330

<210> SEQ ID NO 39
<211> LENGTH: 333
<212> TYPE: PRT
<213> ORGANISM: Saccharomyces cerevisiae

<400> SEQUENCE: 39

Phe Arg Pro Asn Gln Leu Glu Ala Val Asn Ala Thr Leu Gln Gly Lys
1               5                   10                  15
Asp Val Phe Val Leu Met Pro Thr Gly Gly Lys Ser Leu Cys Tyr
                20                  25                  30
Gln Leu Pro Ala Val Val Lys Ser Gly Lys Thr His Gly Thr Thr Ile
                35                  40                  45
Val Ile Ser Pro Leu Ile Ser Leu Met Gln Asp Gln Val Glu His Leu
    50                  55                  60
Leu Asn Lys Asn Ile Lys Ala Ser Met Phe Ser Ser Arg Gly Thr Ala
65                  70                  75                  80
Glu Gln Arg Arg Gln Thr Phe Asn Leu Phe Ile Asn Gly Leu Leu Asp
                85                  90                  95
Leu Val Tyr Ile Ser Pro Glu Met Ile Ser Ala Ser Glu Gln Cys Lys
                100                 105                 110
Arg Ala Ile Ser Arg Leu Tyr Ala Asp Gly Lys Leu Ala Arg Ile Val
                115                 120                 125
Val Asp Glu Ala His Cys Val Ser Asn Trp Gly His Asp Phe Arg Pro
    130                 135                 140
Asp Tyr Lys Glu Leu Lys Phe Phe Lys Arg Glu Tyr Pro Asp Ile Pro
145                 150                 155                 160
Met Ile Ala Leu Thr Ala Thr Ala Ser Glu Gln Val Arg Met Asp Ile
                165                 170                 175
Ile His Asn Leu Glu Leu Lys Glu Pro Val Phe Leu Lys Gln Ser Phe
                180                 185                 190
Asn Arg Thr Asn Leu Tyr Tyr Glu Val Asn Lys Lys Thr Lys Asn Thr
                195                 200                 205
Ile Phe Glu Ile Cys Asp Ala Val Lys Ser Arg Phe Lys Asn Gln Thr
    210                 215                 220
Gly Ile Ile Tyr Cys His Ser Lys Lys Ser Cys Glu Gln Thr Ser Ala
225                 230                 235                 240
Gln Met Gln Arg Asn Gly Ile Lys Cys Ala Tyr Tyr His Ala Gly Met
                245                 250                 255
Glu Pro Asp Glu Arg Leu Ser Val Gln Lys Ala Trp Gln Ala Asp Glu
                260                 265                 270
Ile Gln Val Ile Cys Ala Thr Val Ala Phe Gly Met Gly Ile Asp Lys
    275                 280                 285
Pro Asp Val Arg Phe Val Tyr His Phe Thr Val Pro Arg Thr Leu Glu
                290                 295                 300
Gly Tyr Tyr Gln Glu Thr Gly Arg Ala Gly Arg Asp Gly Asn Tyr Ser
305                 310                 315                 320
Tyr Cys Ile Thr Tyr Phe Ser Phe Arg Asp Ile Arg Thr
```

```
                        325                 330

<210> SEQ ID NO 40
<211> LENGTH: 332
<212> TYPE: PRT
<213> ORGANISM: Homo sapiens

<400> SEQUENCE: 40

Phe Arg Pro Leu Gln Leu Glu Thr Ile Asn Val Thr Met Ala Gly Lys
1               5                   10                  15

Glu Val Phe Leu Val Met Pro Thr Gly Gly Lys Ser Leu Cys Tyr
            20                  25                  30

Gln Leu Pro Ala Leu Cys Ser Asp Gly Phe Thr Leu Val Ile Cys Pro
        35                  40                  45

Leu Ile Ser Leu Met Glu Asp Gln Leu Met Val Leu Lys Gln Leu Gly
    50                  55                  60

Ile Ser Ala Thr Met Leu Asn Ala Ser Ser Lys Glu His Val Lys
65                  70                  75                  80

Trp Val His Ala Glu Met Val Asn Lys Asn Ser Glu Leu Lys Leu Ile
                85                  90                  95

Tyr Val Thr Pro Glu Lys Ile Ala Lys Ser Lys Met Phe Met Ser Arg
            100                 105                 110

Leu Glu Lys Ala Tyr Glu Ala Arg Arg Phe Thr Arg Ile Ala Val Asp
        115                 120                 125

Glu Val His Cys Cys Ser Gln Trp Gly His Asp Phe Arg Pro Asp Tyr
    130                 135                 140

Lys Ala Leu Gly Ile Leu Lys Arg Gln Phe Pro Asn Ala Ser Leu Ile
145                 150                 155                 160

Gly Leu Thr Ala Thr Ala Thr Asn His Val Leu Thr Asp Ala Gln Lys
                165                 170                 175

Ile Leu Cys Ile Glu Lys Cys Phe Thr Phe Thr Ala Ser Phe Asn Arg
            180                 185                 190

Pro Asn Leu Tyr Tyr Glu Val Arg Gln Lys Pro Ser Asn Thr Glu Asp
        195                 200                 205

Phe Ile Glu Asp Ile Val Lys Leu Ile Asn Gly Arg Tyr Lys Gly Gln
    210                 215                 220

Ser Gly Ile Ile Tyr Cys Phe Ser Gln Lys Asp Ser Glu Gln Val Thr
225                 230                 235                 240

Val Ser Leu Gln Asn Leu Gly Ile His Ala Gly Ala Tyr His Ala Asn
                245                 250                 255

Leu Glu Pro Glu Asp Lys Thr Thr Val His Arg Lys Trp Ser Ala Asn
            260                 265                 270

Glu Ile Gln Val Val Ala Thr Val Ala Phe Gly Met Gly Ile Asp
        275                 280                 285

Lys Pro Asp Val Arg Phe Val Ile His His Ser Met Ser Lys Ser Met
    290                 295                 300

Glu Asn Tyr Tyr Gln Glu Ser Gly Arg Ala Gly Arg Asp Asp Met Lys
305                 310                 315                 320

Ala Asp Cys Ile Leu Tyr Tyr Gly Phe Gly Asp Ile
                325                 330

<210> SEQ ID NO 41
<211> LENGTH: 320
<212> TYPE: PRT
<213> ORGANISM: Homo sapiens
```

-continued

```
<400> SEQUENCE: 41

Gln Leu Glu Ala Ile Asn Ala Ala Leu Leu Gly Glu Asp Cys Phe Ile
1               5                   10                  15

Leu Met Pro Thr Gly Gly Lys Ser Leu Cys Tyr Gln Leu Pro Ala
            20                  25                  30

Cys Val Ser Pro Gly Val Thr Val Ile Ser Pro Leu Arg Ser Leu
            35                  40                  45

Ile Val Asp Gln Val Gln Lys Leu Thr Ser Leu Asp Ile Pro Ala Thr
50                  55                  60

Tyr Leu Thr Gly Asp Lys Thr Asp Ser Glu Ala Thr Asn Ile Tyr Leu
65                  70                  75                  80

Gln Leu Ser Lys Lys Asp Pro Ile Ile Lys Leu Leu Tyr Val Thr Pro
                85                  90                  95

Glu Lys Ile Cys Ala Ser Asn Arg Leu Ile Ser Thr Leu Glu Asn Leu
            100                 105                 110

Tyr Glu Arg Lys Leu Leu Ala Arg Phe Val Ile Asp Glu Ala His Cys
        115                 120                 125

Val Ser Gln Trp Gly His Asp Phe Arg Gln Asp Tyr Lys Arg Met Asn
130                 135                 140

Met Leu Arg Gln Lys Phe Pro Ser Val Pro Val Met Ala Leu Thr Ala
145                 150                 155                 160

Thr Ala Asn Pro Arg Val Gln Lys Asp Ile Leu Thr Gln Leu Lys Ile
                165                 170                 175

Leu Arg Pro Gln Val Phe Ser Met Ser Phe Asn Arg His Asn Leu Lys
            180                 185                 190

Tyr Tyr Val Leu Pro Lys Lys Pro Lys Val Ala Phe Asp Cys Leu
        195                 200                 205

Glu Trp Ile Arg Lys His His Pro Tyr Asp Ser Gly Ile Ile Tyr Cys
210                 215                 220

Leu Ser Arg Arg Glu Cys Asp Thr Met Ala Asp Thr Leu Gln Arg Asp
225                 230                 235                 240

Gly Leu Ala Ala Leu Ala Tyr His Ala Gly Leu Ser Asp Ser Ala Arg
                245                 250                 255

Asp Glu Val Gln Gln Lys Trp Ile Asn Gln Asp Gly Cys Gln Val Ile
            260                 265                 270

Cys Ala Thr Ile Ala Phe Gly Met Gly Ile Asp Lys Pro Asp Val Arg
        275                 280                 285

Phe Val Ile His Ala Ser Leu Pro Lys Ser Val Glu Gly Tyr Tyr Gln
290                 295                 300

Glu Ser Gly Arg Ala Gly Arg Asp Gly Glu Ile Ser His Cys Leu Leu
305                 310                 315                 320

<210> SEQ ID NO 42
<211> LENGTH: 344
<212> TYPE: PRT
<213> ORGANISM: Homo sapiens

<400> SEQUENCE: 42

Cys Leu Lys Met Tyr Phe Gly His Ser Ser Phe Lys Pro Val Gln Trp
1               5                   10                  15

Lys Val Ile His Ser Val Leu Glu Glu Arg Arg Asp Asn Val Ala Val
            20                  25                  30

Met Ala Thr Gly Tyr Gly Lys Ser Leu Cys Phe Gln Tyr Pro Pro Val
        35                  40                  45
```

```
Tyr Val Gly Lys Ile Gly Leu Val Ile Ser Pro Leu Ile Ser Leu Met
 50                  55                  60
Glu Asp Gln Val Leu Gln Leu Lys Met Ser Asn Ile Pro Ala Cys Phe
 65                  70                  75                  80
Leu Gly Ser Ala Gln Ser Glu Asn Val Leu Thr Asp Ile Lys Leu Gly
                     85                  90                  95
Lys Tyr Arg Ile Val Tyr Val Thr Pro Glu Tyr Cys Ser Gly Asn Met
                100                 105                 110
Gly Leu Leu Gln Gln Leu Glu Ala Asp Ile Gly Ile Thr Leu Ile Ala
                115                 120                 125
Val Asp Glu Ala His Cys Ile Ser Glu Trp Gly His Asp Phe Arg Asp
130                 135                 140
Ser Phe Arg Lys Leu Gly Ser Leu Lys Thr Ala Leu Pro Met Val Pro
145                 150                 155                 160
Ile Val Ala Leu Thr Ala Thr Ala Ser Ser Ile Arg Glu Asp Ile
                165                 170                 175
Val Arg Cys Leu Asn Leu Arg Asn Pro Gln Ile Thr Cys Thr Gly Phe
                180                 185                 190
Asp Arg Pro Asn Leu Tyr Leu Glu Val Arg Arg Lys Thr Gly Asn Ile
                195                 200                 205
Leu Gln Asp Leu Gln Pro Phe Leu Val Lys Thr Ser Ser His Trp Glu
                210                 215                 220
Phe Glu Gly Pro Thr Ile Ile Tyr Cys Pro Ser Arg Lys Met Thr Gln
225                 230                 235                 240
Gln Val Thr Gly Glu Leu Arg Lys Leu Asn Leu Ser Cys Gly Thr Tyr
                245                 250                 255
His Ala Gly Met Ser Phe Ser Thr Arg Lys Asp Ile His His Arg Phe
                260                 265                 270
Val Arg Asp Glu Ile Gln Cys Val Ile Ala Thr Ile Ala Phe Gly Met
                275                 280                 285
Gly Ile Asn Lys Ala Asp Ile Arg Gln Val Ile His Tyr Gly Ala Pro
                290                 295                 300
Lys Asp Met Glu Ser Tyr Tyr Gln Glu Ile Gly Arg Ala Gly Arg Asp
305                 310                 315                 320
Gly Leu Gln Ser Ser Cys His Val Leu Trp Ala Pro Ala Asp Ile Asn
                325                 330                 335
Leu Asn Arg His Leu Leu Thr Glu
                340

<210> SEQ ID NO 43
<211> LENGTH: 106
<212> TYPE: PRT
<213> ORGANISM: Homo sapiens

<400> SEQUENCE: 43

Thr Asn Leu His Leu Ser Val Ser Met Asp Arg Asp Thr Asp Gln Ala
 1                   5                  10                  15
Leu Leu Thr Leu Gln Gly Lys Arg Phe Gln Asn Leu Asp Ser Ile
                 20                  25                  30
Ile Ile Tyr Cys Asn Arg Arg Glu Asp Thr Glu Arg Ile Ala Ala Leu
                 35                  40                  45
Leu Arg Thr Cys Leu His Ala Ala Trp Val Pro Gly Ser Gly Arg
                 50                  55                  60
Ala Pro Lys Thr Thr Ala Glu Ala Tyr His Ala Gly Met Cys Ser Arg
65                  70                  75                  80
```

-continued

```
Glu Arg Arg Arg Val Gln Arg Ala Phe Met Gln Gly Gln Leu Arg Val
                85                  90                  95
Val Val Ala Thr Val Ala Phe Gly Met Gly
            100                 105

<210> SEQ ID NO 44
<211> LENGTH: 88
<212> TYPE: PRT
<213> ORGANISM: Escherichia coli

<400> SEQUENCE: 44

Asn Ile Arg Tyr Met Leu Met Glu Lys Phe Lys Pro Leu Asp Gln Leu
1               5                   10                  15
Met Arg Tyr Val Gln Glu Gln Arg Gly Lys Ser Gly Ile Ile Tyr Cys
                20                  25                  30
Asn Ser Arg Ala Lys Val Glu Asp Thr Ala Ala Arg Leu Gln Ser Lys
            35                  40                  45
Gly Ile Ser Ala Ala Tyr His Ala Gly Leu Glu Asn Asn Val Arg
        50                  55                  60
Ala Asp Val Gln Glu Lys Phe Gln Arg Asp Asp Leu Gln Ile Val Val
65                  70                  75                  80
Ala Thr Val Ala Phe Gly Met Gly
                85
```